(12) United States Patent
Ragg

(10) Patent No.: US 11,229,601 B2
(45) Date of Patent: Jan. 25, 2022

(54) DEVICES AND METHODS FOR INJECTABLE VASCULAR SCLEROFOAMS USING A CARRIER MATRIX AND USES THEREOF

(71) Applicant: SWISS VX VENENTHERAPIE UND FORSCHUNG GMBH, Schindellegi Gem Feusisberg (CH)

(72) Inventor: Johann Christof Ragg, Berlin (DE)

(73) Assignee: SWISS VX VENETHERAPIE UND FORSCHUNG GMBH, Schindellegi Gem (CH)

( * ) Notice: Subject to any disclaimer, the term of this patent is extended or adjusted under 35 U.S.C. 154(b) by 0 days.

(21) Appl. No.: 16/417,963

(22) Filed: May 21, 2019

(65) Prior Publication Data
US 2019/0336445 A1    Nov. 7, 2019

Related U.S. Application Data

(62) Division of application No. 15/323,573, filed as application No. PCT/EP2015/065142 on Jul. 2, 2015.

(30) Foreign Application Priority Data

Jul. 30, 2014 (EP) .................................. 14175609

(51) Int. Cl.
| | |
|---|---|
| A61K 9/12 | (2006.01) |
| A61K 9/00 | (2006.01) |
| A61K 35/14 | (2015.01) |
| A61K 31/045 | (2006.01) |
| A61K 31/185 | (2006.01) |
| A61K 31/45 | (2006.01) |
| A61K 31/255 | (2006.01) |
| A61K 31/08 | (2006.01) |

(52) U.S. Cl.
CPC .............. *A61K 9/122* (2013.01); *A61K 9/0019* (2013.01); *A61K 31/045* (2013.01); *A61K 31/08* (2013.01); *A61K 31/185* (2013.01); *A61K 31/255* (2013.01); *A61K 31/45* (2013.01); *A61K 35/14* (2013.01)

(58) Field of Classification Search
CPC .............................. A61K 9/122; A61K 9/0019
See application file for complete search history.

(56) References Cited

U.S. PATENT DOCUMENTS

| | | |
|---|---|---|
| 4,466,442 A | 8/1984 | Hilmann et al. |
| 7,357,336 B2 | 4/2008 | Osman et al. |
| 8,091,801 B2 | 1/2012 | Osman et al. |
| 2002/0031476 A1 | 3/2002 | Trevino et al. |
| 2002/0077589 A1 | 6/2002 | Tessari |
| 2006/0074386 A1 | 4/2006 | Wollmann |
| 2007/0003489 A1 | 1/2007 | Wright et al. |
| 2010/0099778 A1* | 4/2010 | Wright ................ B01F 3/04446 514/723 |

FOREIGN PATENT DOCUMENTS

| | | |
|---|---|---|
| CN | 103800278 | 5/2014 |
| EP | 2656869 | 10/2013 |
| WO | WO-95/00120 | 1/1995 |
| WO | WO-03/099681 | 12/2003 |
| WO | WO-2005/048976 | 6/2005 |
| WO | WO-2006/037735 | 4/2006 |
| WO | WO-2016/001378 | 1/2016 |

OTHER PUBLICATIONS

Geroulakos, G., Foam sclerotherapy for the management of varicose veins: a critical reappraisal, Phlebolymphology. 2006; 13(4):202-6.

Hamei-Desnos, C et al., Evaluation of the Efficacy of Polidocanol in the Form of Foam Compared with Liquid Form in Sclerotherapy of the Greater Saphenous Vein: Initial Results. Dermatol Surg. 2003; 29(12):1170-1175.

Maurins, U. et al., Distribution and prevalence of reflux in the superficial and deep venous system in the general population—results from the Bonn Vein Study, Germany. J Vasc Surg. 2008; 48(3):680-687.

Yamaki, T. et al., Comparative study of duplex-guided foam sclerotherapy and duplex-guided liquid sclerotherapy for the treatment of superficial venous insufficiency. Dermatol Surg. 2004; 30 (5): 718-22.

International Search Report and Written Opinion dated Aug. 20, 2015 by the International Searching Authority for International Application No. PCT/EP2015/065142, which was filed on Jul. 2, 2015 and published as WO/2016/001378 on Jan. 7, 2016 (Applicant—Swiss VX Venentherapie und Forschung GmbH) (14 pages).

(Continued)

*Primary Examiner* — Gina C Justice
(74) *Attorney, Agent, or Firm* — Ballard Spahr LLP

(57) ABSTRACT

The invention relates in particular to an injectable sclerosant drug foam comprising: (i) a matrix; (ii) at least one fluid; (iii) at least one sclerosant drug; (iv) a medical gas or medical gas mixture acceptable for intravenous use, (v) wherein said matrix has physical properties, which are comparable to denatured blood, wherein the denatured blood is obtainable from a fresh human venous whole blood sample of 1 ml volume, which is heated in a cylindrical polyethylene container with 3 mm inner diameter and 3.4 mm outer diameter for about 0.5 min. to about 10 min. at a temperature of about between 70° C. and 100° C. and/or (vii) said level of denaturation is defined by the change of red-colored hemoglobin to brown as an indicator, wherein $Fe^{2+}$ is reduced to $Fe^{3+}$ in the hemoglobin complex to a degree of at least 80%, preferably 90% and even more preferably 95%.

21 Claims, 13 Drawing Sheets

(56) References Cited

OTHER PUBLICATIONS

International Preliminary Report on Patentability dated Jan. 3, 2017 by the International Searching Authority for International Application No. PCT/EP2015/065142, which was filed on Jul. 2, 2015 and published as WO/2016/001378 on Jan. 7, 2016 (Applicant—Swiss VX Venentherapie und Forschung GmbH) (10 pages).

* cited by examiner

Figure 3B:
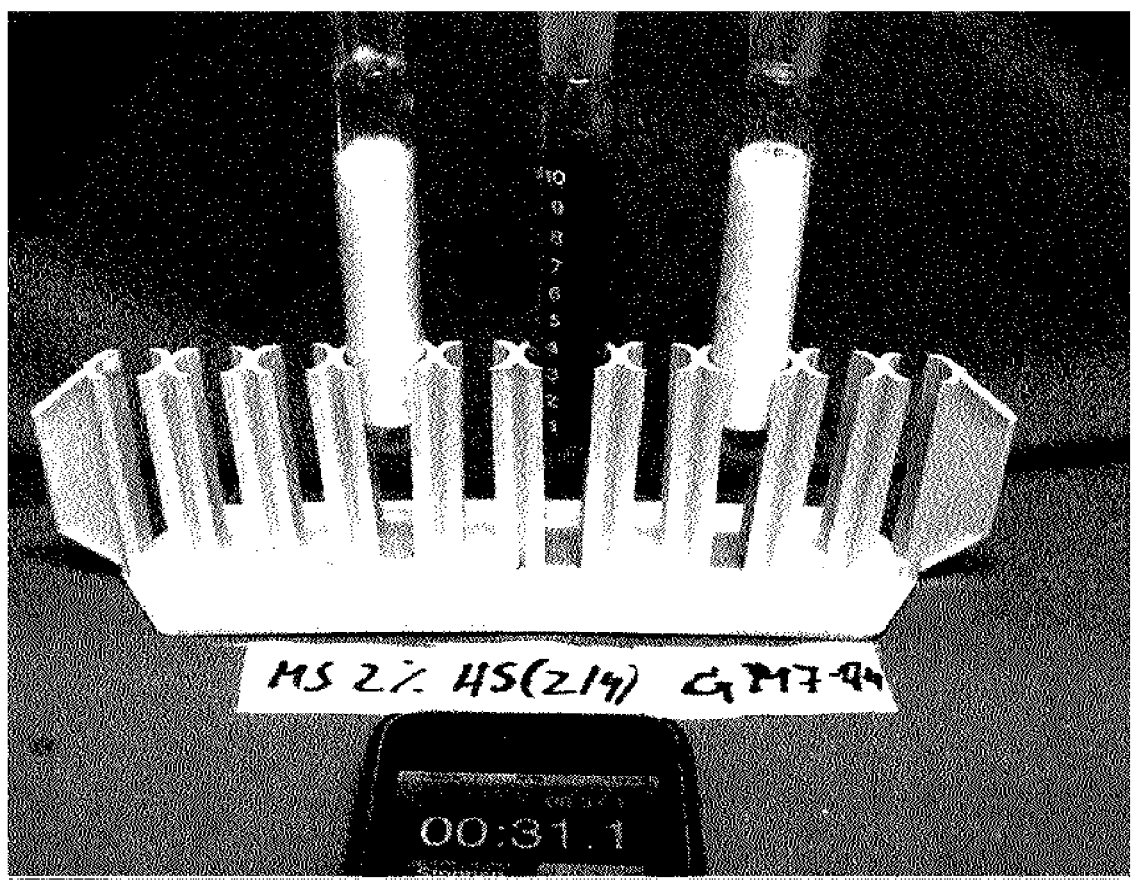

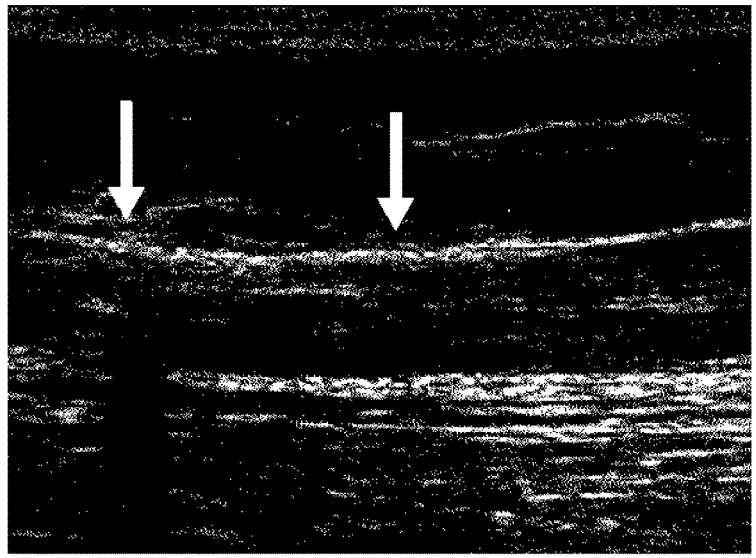
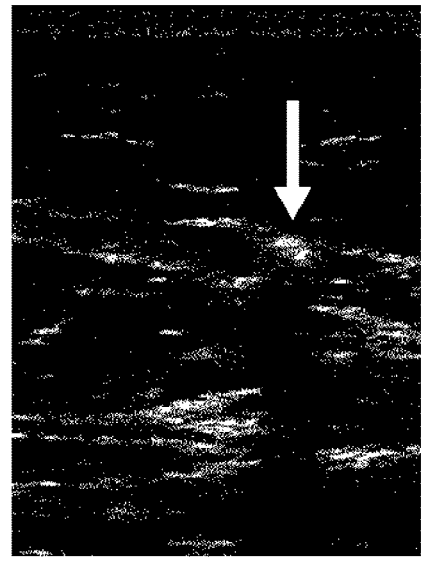
FIG. 2A
FIG. 2B
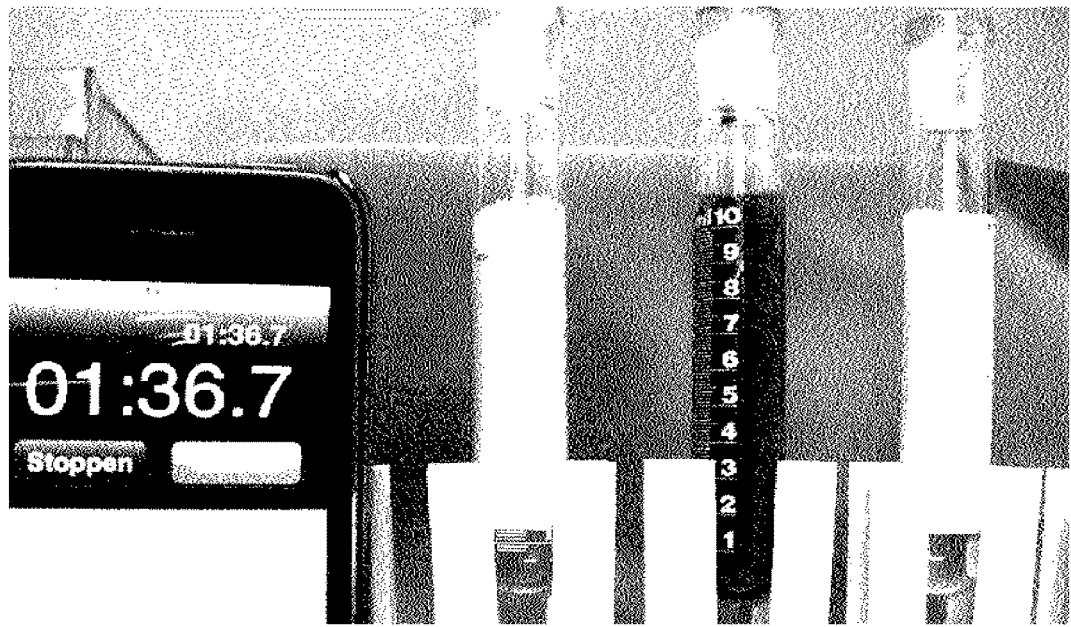
FIG. 3A

DEVICES AND METHODS FOR INJECTABLE VASCULAR SCLEROFOAMS USING A CARRIER MATRIX AND USES THEREOF

CROSS-REFERENCE TO RELATED APPLICATIONS

This application is a continuation of U.S. application Ser. No. 15/323,573, filed Jan. 3, 2017, which is a National Stage Entry of PCT/EP2015/065142, filed Jul. 2, 2015, which claims benefit of European Application No. 14175609.8, filed Jul. 3, 2014, each of which are hereby incorporated herein by reference in their entirety.

FIELD OF THE INVENTION

The present invention relates to the field of medicine and therapeutics, particularly vein therapeutics, more particularly to the field of sclerotherapy. Furthermore the invention relates to sclerosant drugs, particularly sclerosant drug foams and methods for the production of sclerosant drug foams and uses thereof.

BACKGROUND OF THE INVENTION

Blood vessels in humans and animals are grouped as arterial and venous, determined by whether the blood in it is flowing away from (arterial) or toward (venous) the heart. Veins collect blood from organs, muscle, connective tissue and skin. Venous blood has a low content of oxygen and nutrients, but enriched in carbon dioxide and final metabolism products.

Caused by acquired functional weakness due to lack of activity or by congenital defects, a large number of people show venous congestion in the legs. Congestion means a presence of blood above the physiological level. If no change in habits occurs, congestion turns into insufficiency within few years. Insufficiency means that vein valves become incompetent, resulting in a reversed blood flow. In a vicious circle insufficiency further increases venous blood congestion, and the disease increases with time. Varicose veins develop from insufficiency, they are superficial veins which have been stressed by an overload of blood for years and therefore show large diameters and a tortuous course. Incompetent leg veins are found in 21-25% of people aged 35 or above, and spider veins even in 50% (Uldis Maurins, Barbara H. Hoffmann, Christian Lösch, Karl-Heinz Jöckel, Eberhard Rabe, Felicitas Pannier: Distribution and prevalence of reflux in the superficial and deep venous system in the general population—results from the Bonn Vein Study, Germany. Journal of Vascular Surgery, Vol 48, Issue 3, September 2008, 680-687).

Beside the cosmetic issues, insufficient and varicose veins lead to major complications, due to the congestion and the poor circulation through the affected limb. The complications comprise pain, heaviness, inability to walk or stand for long hours, skin inflammation, skin damage predisposing skin loss or skin ulcers especially near the ankle, usually referred to as venous ulcers, severe bleeding from minor trauma, blood clotting within affected veins (thrombophlebitis, thrombosis, embolic events). Some vascular malformations like Klippel-Trénaunay-Weber of syndrome also go along with varicose veins.

For dilated veins, surgical removal of the target structure, e.g. varicose veins, has been a widely used therapy for decades. However, like all surgical treatments this may be accompanied by several, partially serious adverse effects, i.e. damaging of adjacent arteries, nerves or lymphatic vessels, generation of wounds and cicatrices, wound infections, or intolerance of the patient for narcotic drugs. Furthermore, the tissue damage going along with every surgery, in particular in junction regions like the groin or the popliteal area seems to induce the growth of new, but diseased veins.

As an alternative to surgical removal, different ways of endovenous closure methods have been developed, allowing minimal-invasive treatments with a very low complication rate.

The term endovenous means, therapy is performed by catheter access through the venous system, and within the diseased vein. Catheters are small-lumen tubes, inserted via a single puncture site. The aim of these methods is the permanent closure of the treated vein or vein segment. The effect may be obtained by thermal treatment (e.g. by laser, radiofrequency, steam), or by injection of chemical agents (fluids, foams, adhesives). Due to the use of catheters and probes, thermal treatment and gluing is restricted to relatively linear vessels while chemical agents may also reach curved and tortuous segments and branched or reticular veins.

The effect of all the named endovascular methods applied to peripheral veins is to permanently denature functional proteins in the innermost tissue layer, the so-called endothelial cell layer. Said denaturing process triggers the aggregation of blood cells, in particular thrombocytes, at the vein wall. It is a kind of artificial thrombosis which occludes the vein. In contrary to incidental thrombosis which may be hoped to resolve, in the therapeutic approach the aim is to completely denaturize all the endothelium in the segment to treat. Only parts of the vessel wall sufficiently reached by the thermal or sclerotic effect can be expected to close permanently, while undamaged endothelium will revitalize and lead to recurrent pathologic blood flow.

All endovenous procedures are associated with a local vein spasm, due to effects passing the endothelium layer and reaching the muscular layer. Spasm means a contraction of muscular cells, leading to an immediate reduction of the vein diameter. The vein spasm trigger by endovenous techniques is in general not lasting longer than minutes above the activity of the trigger. However, it would be desirable to maintain the spasm or the by spasm reduced vein size as long as it takes the blood within the treated vein to clot, organize and fix the vein size. Occlusion and decrease in vessel diameter are the two most important aims of this kind of therapy. A real initial shrinking could only be obtained by an effect reaching deep into the muscular layer with a permanent shortening of fibers. On the other hand, with increasing effects on the muscular layer the danger of vein perforation increases, and so does pain during and after treatment as there are only micrometers distance to the highly innervated outer wall layer called adventitia. All so far existing sclerosants or thermo-occlusive techniques do not solve these problems and therefore are of limited value. The use of adhesives could be a future solution, but techniques are still insufficient and effective biocompatible and totally biodegradable are not yet available for intravascular use.

Simple sclerotherapy is known for more than 60 years. Today's common liquid sclerosant drugs are e.g. alcohols with detergent properties like polidocanol or sodium tetradecyl sulphate. In the eldest modality, the liquid sclerosant drug is injected via metallic cannulas directly into the vessels. Due to its high flowability the liquid sclerosant drug flows with the blood stream and quickly mixes with blood, soon reaching ineffective dilutions. Blood protein bindings additionally limit the effect of fluid sclerosant agents.

In order to circumvent some drawbacks of the liquid sclerosant drugs, it has been established to produce a sclerosant foam by mixing the liquid sclerosant drug with a gas. The resulting sclerosant drug foam is injected into the target structure, e.g. the varicose vein. For foaming the sclerosant drug (e.g. sodium tetradecyl sulfate or polidocanol) is mixed with sterile air or a physiological gas (carbon dioxide, oxygen) in a syringe or by using mechanical pumps.

In the literature, the terms "foam sclerotherapy", "sclerofoam", "microfoam" and "sclerosant drug foam" are used. Sclerofoam can be produced by mixing liquid sclerosant with a medical gas like $O_2$ or $CO_2$, or room air, using the TESSARI method by 10-20 times to- and fro injection from one syringe to another via stopcock or Luer-connector, by shaking a syringe, simultaneous aspiration of fluid and gas, or mechanically by pumps, positive or negative pressure devices, perforated outlets or valves, or by propellers or rotating brushes (GEROULAKOS G.: Foam sclerotherapy for the management of varicose veins: a critical reappraisal, Phlebolymphology Vol 13, No. 4 (2006) p 181-220).

If injected properly, foam will replace blood totally for a certain time, varying from seconds to a few minutes. In this time, the contact to the vein wall is more intense than in case of a liquid bolus just passing by. The chemical reaction of the sclerosant on the endothelium (innermost wall layer) will expand to the media layer and trigger muscular spasms, which may be more intense than in the case of fluid sclerosants of the same chemical concentration.

Foaming increases the surface area of the drug. Due its higher stiffness and viscosity, the sclerosant drug foam is more efficacious in causing sclerosis than the liquid sclerosant drug (Thickening of the vessel wall and sealing off the blood flow; Yamaki T, Nozaki M, Iwasaka S.: Comparative study of duplex-guided foam sclerotherapy and duplex-guided liquid sclerotherapy for the treatment of superficial venous insufficiency, 2004, Dermatol Surg 30 (5): 718-22; Evaluation of the Efficacy of Polidocanol in the Form of Foam Compared With Liquid Form in Sclerotherapy of the Greater Saphenous Vein: Initial Results; Claudine Hamel-Desnos, Philippe Desnos, Jan-Christoph Wollmann, Pierre Ouvry, Serge Mako, François-Andre Allaer, Dermatol Surg 29 (12): 1170-1175 (2003); WO 95/00120 J. Cabrera et al. 1995).

Figure 1B:
Figure 1A:

Besides the viscosity, an important property of sclerofoam is its visibility in ultrasound scans due to the contents of gas which reflects the sound energy (FIG. 1). Therefore, foam injections can be ultrasound monitored and the dosage can be adapted to the individual requirements, which is not feasible with fluid sclerosants as their signal does not differ from fluid blood.

However, the gas may accumulate and lead to acoustic shadows, hiding relevant anatomic structures. It is rarely possible to tell if all the lumen is completely filled with foam, or if there is just a layer of foam floating on blood (FIG. 1).

Although some ultrasound contrast media have been developed, e.g. US 20020031476 A1 disclosing a stabilized gas emulsion containing phospholipids for ultrasound contrast enhancement, or U.S. Pat. No. 4,466,442 A disclosing carrier liquid solutions for the production of gas microbubbles as contrast medium for ultrasonic diagnostics using tensides, such media have not been used to optimize sclerotherapy.

In clinical practice the majority of sclerotherapies are not complete in the sense of total circumferential endothelium denaturation. For example, in case of slow injection, and as well in case of complex and tortuous varicose formations which limit the injection velocity, foam will float on blood instead of replacing it. Only partial denaturation of the endothelium will be achieved. Trials have shown that even by axially turning the patient for 180 degrees the foam will not sufficiently reach the opposite vein walls.

There are some more drawbacks of common sclerofoam: If an injection is performed too fast, foam will also spread to healthy veins and may lead to unintended closures or thrombosis. When a vein shrinks after foam injection by foam-induced spasm to a percentage of its original diameter, significant amounts of foam will migrate to diseased or healthy neighbouring vessels with the same consequence. Common foams are mechanically too weak to resist and stay in place.

In the initial experience it was most welcome that the foam collapses within a short time, coming from the idea of rapid elimination. However, due to rapid foam collapse all the chemicals are transferred to the circulation within minutes which may lead to side effects like bronchospasms or vision disorders. The lack of stability seems to be the most important drawback of common sclerosant foams.

The process of sclerotherapy in detail is this: If sclerofoam is injected into a diseased vein, it replaces the blood, touches the vein wall and triggers a vein spasm. This can be felt during foam injection as an increase of resistance, which is regarded as a sign to stop the injection. As native side branches now have low flow resistance compared to the spastic target vein, a further injection would go there which is normally not intended. If a foam injection is stopped in time, undisturbed collateral flow will dilute small amounts of overdosage and prevent side effects.

The musculature of spastic veins will relax within 5-60 minutes after foam injection, and remainders of common foam will at the latest then be washed off. When the vein spasm vanishes, blood will return to the target vessel. Although by external compression (stockings, bandages) the amount of blood returning to the treated vein can be reduced to some extent, it cannot be avoided effectively or even completely.

The vein will close within several hours to few days after foam injection. However, vein closure may not only occur due to endothelium denaturation, but also if just parts of the endothelium have been denaturized, as occlusive thrombus may form there and reduce or stop the blood flow. Then further parts of vein segment will close due to thrombosis, which will appear as a success. However, all thrombotic occlusion in regions without complete endothelium denaturation is reversible as endothelium is still vital. Therefore, any closure proved by ultrasound examination within days or weeks post treatment does in no way prove endothelium destruction or a success of foam treatment. If closure of this kind occurs, it will not be complete, not stable, or show early relapse. In fact, many cases of "relapse" within the first years represent failed primary endothelium destruction, caused by insufficient foam distribution.

In the case of incomplete endothelium destruction, thrombotic and recanalisation phases will compete and clinically appear as painful phlebitis. This is often clinically more intense than general inflammatory reactions after endothelium denaturation.

An optimized foam should be able to completely replace blood in a diseased vein due to much higher viscosity, and thus solve the problem of incomplete foam treatments.

At the point of primary vein closure, there is no more perfusion in this vessel, and the pathological backward flow is eliminated. This is the same hemodynamic effect like achieved by surgery ("elimination of reflux"), and it is the main endpoint of treatment quality.

In contrary to surgery, the vein is still in place. For optimal results, it should now be neither visible nor palpable. The patient should not feel its existence when moving or at rest. However, this aim is not reached for larger veins by today's sclerotherapies. The reason is that these techniques only trigger a complex process of shrinking and organization which will take weeks to many months, depending on the size of the vein.

Frequently, the vein regains the same diameter it had before treatment. The total amount of clotted blood contained in the vein at the time of total occlusion will determine the duration and symptoms of the organization process. Clotted blood within the vessel will have to be removed by metabolism, performing a change from a large thrombotic vein to a small string of connective tissue. As a fact, the incidence of unwanted side effects like painful inflammations, brownish discolorations, long-lasting indurations and still visible varicose veins rises with the vein diameter and may occur in up to 80% of the treated cases.

It is assumed that the effect of sclerofoam treatments depends on its physical stability. The stability of foam sclerosants is appreciated by the so called volume half life, telling the time until 50% of the foam is collapsed. Common volume half lives of polidocanol microfoams made in silicone-free plastic syringes are 60-180 s. Using glass syringes and forced foaming procedures by to- and fro injections from one syringe to another, volume half times of 210 s can be obtained and much better results are observed after applying this kind of foam.

So, one major aim for an optimized foam sclerosant is, to obtain a prolonged volume half life. If achievable, also the effect on the endothelium would be stronger. Using the same concentration of sclerosant, the denaturing effect would grow with the time of interaction to the vessel wall. The dosage of the chemical agent could potentially be reduced.

As sclerofoams of prior kind disintegrate quickly, the rate of unwanted side effects is high: Thrombosis (occlusion of deep veins) caused by migrated foam appears in a rate of up to 4%. Unwanted closure of healthy epifascial veins is estimated at up to 20%, while the clinical sequelae are yet unknown.

Most of conventional foam therapies require several sessions for the aimed success. Sometimes, treatment plans consist of 5-10 visits. This is time consuming for patient and physician. Also the wearing time of bandages or stockings is prolonged.

Summarizing, when treating diseased veins with common sclerotherapy techniques, many attempts are incomplete, induce relevant side effects or frequently show relapse. The diseased vein will not be permanently closed at the end of the procedure. There may remain a space consuming and symptomatic structure for weeks to months. It would be advantageous to have means for instantaneous and permanent closure of diseased veins.

There have been several attempts to improve foam sclerotherapy. WO 2006/037735 A1 discloses a device for producing a medical foam by using sealed containers for sterile sclerosant and sterile gas, which contributes to hygienic aspects and simplification of the procedure as gas and sclerosant do not have to be aspirated from larger containers. However the insufficient physical features of the foam remain unchanged.

Improved therapeutic sclerofoams generated by pressurized gas are disclaimed in U.S. Pat. No. 8,091,801 B2. However, also these foams hardly reach volume half times above a few minutes.

The generation of therapeutic microfoam with gases like carbon dioxide or xenon has been proposed to reduce side effects induced by large amounts of slow resorbable gases like nitrogen, e.g. disclaimed in U.S. Pat. No. 7,357,336 B2. However, such side effects are rarely seen when applying foam volumes less than 10 cc per session. The technical foam properties are not significantly changed, in particular the half-live remains insufficiently short.

To overcome all the drawbacks of sclerosant drugs and sclerosant drug foams of prior art the ideal sclerosant substance has to fulfill a variety of features: It should have a significantly increased consistency or stiffness to fill the target vein completely and precisely. The viscosity should be adjustable for different approaches, e.g. less viscous for injection in small and long cavities, or highly viscous for short or large cavities. It should allow injection via catheters. It should induce long lasting spasms of the target structures. After injection into the target structure foam should remain within said structure until its completed occlusion. Foam within the target vein should dissolve slowly to reduce the inflow of chemical agents to the circulation. For this purpose, the foam should have a volume half-life of hours to days. It should be clearly visible in ultrasound scans but, nevertheless, it should not produce relevant acoustic shadows and always show all relevant tissue and vessel structures. It furthermore has to be safe for application in humans, in particular rates for unwanted side effects like thrombosis or embolism should be significantly lower than in former foam techniques and products. It finally should not contain other chemicals than the sclerosant, and should be 100% biocompatible and biodegradable. Thus the problem is to provide a sclerosant drug foam with the desired properties.

BRIEF DESCRIPTION OF THE INVENTION

The present invention relates to a sclerosant drug foam comprising a matrix. Preferably said matrix comprises denatured blood, preferably prepared from an autologous blood sample, dispersed with at least one fluid and at least one sclerosant drug, and foamed with a gas useable for intravenous application.

The invention relates in particular to an injectable sclerosant drug foam comprising:
(i) a matrix;
(ii) at least one fluid;
(iii) at least one sclerosant drug;
(iv) a medical gas or medical gas mixture acceptable for intravenous use,
(v) wherein said matrix has physical properties, which are comparable to denatured blood, wherein the denatured blood is obtainable from a fresh human venous whole blood sample of 1 ml volume, which is heated in a cylindrical polyethylene container with 3 mm inner diameter and 3.4 mm outer diameter for about 0.5 min. to about 10 min. at a temperature of about between 70° C. and 100° C. and/or
(vii) said level of denaturation is defined by the change of red-colored hemoglobin to brown as an indicator, wherein $Fe^{2+}$ is reduced to $Fe^{3+}$ in the hemoglobin complex to a degree of at least 80%, preferably 90% and even more preferably 95%.

In a particular embodiment the invention relates in particular to an injectable sclerosant drug foam comprising:

(i) denatured blood;
(ii) at least one fluid;
(iii) at least one sclerosant drug;
(iv) a medical gas or medical gas mixture acceptable for intravenous use,
(v) wherein the denatured blood is characterized by a certain level of denaturation,
(vi) wherein said level of denaturation is defined by the color of the denatured blood and said color of denatured blood is comparable to or identical to blood being denatured as follows:
   a fresh human venous whole blood sample of 1 ml volume is heated in a cylindrical polyethylene container with 3 mm inner diameter and 3.4 mm outer diameter for about 0.5 min. to about 10 min. at a temperature of about between 70° C. and 100° C. and/or
(vii) said level of denaturation is defined by the change of red-colored hemoglobin to brown as an indicator, wherein $Fe^{2+}$ is reduced to $Fe^+$ in the hemoglobin complex to a degree of at least 80%, preferably 90% and even more preferably 95%.

As there are multiple ways to denature human blood, the desired effect is defined by one particular embodiment of the invention, obtaining denaturation of a whole blood sample of 1 ml volume in a cylindrical polyethylene container with 3 mm inner diameter and 3.4 mm outer diameter, heated by circumferential contact to a heating element for 0.5-10 min. at temperatures between 75 and 100° C., using the change of the red color of hemoglobin to brown during heat exposure as an indicator for the appropriate degree of denaturation. The denaturation required for this specific purpose may be obtained by heat conduction, heat or energy radiation or by mixing with heated fluids or gases.

In a preferred embodiment the denatured blood corresponds to a whole blood sample of 1 ml volume in a cylindrical polyethylene container with 3 mm inner diameter and 3.4 mm outer diameter, heated by circumferential contact to a heating element for 3 min. at 81° C.

Dispersion is obtained by mixing denatured blood with at least one fluid and at least one sclerosant medium, using mechanical forces like acceleration and slow down of fluid beams to obtain small particles disperged in fluid.

The sclerosant foam is obtained by mixing the dispersion including at least one sclerosant agent with a medical gas like $O_2$ or $CO_2$ or compositions thereof.

The invention further relates to a method for the production of a sclerosant drug foam based on a matrix comprising the following steps:
(a) generation of a stabile matrix
(b) dispersing the matrix within a pharmaceutically acceptable liquid by applying forces to obtain a particle size of 5-300 μm, preferably <120 μm, even more preferably <50 μm wherein in one embodiment the pharmaceutically acceptable liquid is or comprises said at least one sclerosant drug;
(c) mixing the dispersion with at least one sclerosant drug if not performed in step (b)
(d) optionally filtering the suspension or emulsion to exclude particles larger than 50-120 μm;
(e) foaming the dispersion with a gas which is acceptable for intravenous use;

The invention further relates to a method for the production of a sclerosant drug foam based on a human blood matrix preferably made from autologous blood comprising the following steps:

(a) denaturation of a blood sample
(b) dispersing denatured blood within a pharmaceutically acceptable liquid by applying forces to obtain a particle size of 5-300 μm, preferably <120 μm, even more preferably <50 μm wherein in one embodiment the pharmaceutically acceptable liquid is or comprises said at least one sclerosant drug;
(c) mixing the dispersion with at least one sclerosant drug if not performed in step (b)
(d) optionally filtering the suspension or emulsion to exclude particles larger than 50-120 μm;
(e) foaming the dispersion with a gas which is acceptable for intravenous use;

The invention also relates to a device (FIG. 5) for the production of a sclerosant drug foam comprising:
(a) a catheter for blood sampling and foam distribution (1),
(b) a first container (4) for blood collection and denaturation,
(c) an external element for denaturation by heat, radiation or chemicals (6) to be physically or thermically connected to the first container,
(d) a second container (10) for at least one fluid and/or at least one sclerosant agent,
(e) a unit (7a) to apply mechanical force to the contents of the first and/or second container for mixing/dispersing,
(f) a chopping element (7b),
(g) a filter element (13),
(h) a third container to hold the dispersion (14),
(i) a fourth container containing a medical gas (18),
(j) a unit (16) to apply mechanical force to the contents of the third and/or fourth container for foaming,
(j) two-way switches, one-way valves, single stop cocks or combinations thereof (2, 3, 9, 15, 17),
(k) auxiliary access to the device, e.g. to apply negative or positive pressure, or to supply fluids or gases (4a, 8, 11a, 11b, 19)
(l) connection elements connecting all modular parts.

Here, an amount of blood is taken from the target vein through the catheter (1) and guided to the first container (4) where the blood is denatured by help of the denaturation unit (6). The denatured blood is mixed with a fluid and/or sclerosant agent from a second container (10) to form a dispersion by application of mechanical forces (7). If the mixing procedure alone would leave particles above 120 μm, a chopping unit (7b) is added and the dispersion passed once or several times. To ensure no particles above 120 μm are present in the dispersion, it may be filtered (13) and guided to a third container (14). Then a connection to a fourth container (18) providing a medical gas is established and a foam produced by mixing the gas with the dispersion by applying mechanical force (16). The foam is finally provided in one of the containers (14, 18) and transferred to the diseased vein via catheter (1).

The invention further relates to a kit for the production of the sclerosant drug foam comprising:
(i) a device for sterile denaturing of autologous blood
(ii) optionally at least one liquid
(iii) optionally at least one sclerosant agent, if not included in (ii)
(iv) optionally a medical gas like $CO_2$ and/or $O_2$ or a mixture thereof
(v) optionally one or several catheters for venous access and foam deployment The invention further relates to a method of treating venous insufficiency using a sclerosant drug foam based on a matrix of denatured blood, comprising the steps of:

(i) accessing the diseased vein
(ii) preparing the sclerosant drug foam on a basis of denatured blood
(iii) deploying the sclerosant drug foam along the diseased vein

DETAILED DESCRIPTION OF THE INVENTION

The present invention relates to a sclerosant drug foam comprising a matrix. Preferably said matrix comprises denatured blood or has physical properties analogous to denatured blood.

The invention relates in particular to an injectable sclerosant drug foam comprising:
(i) a matrix;
(ii) at least one fluid;
(iii) at least one sclerosant drug;
(iv) a medical gas or medical gas mixture acceptable for intravenous use,
(v) wherein said matrix has physical properties, which are comparable to denatured blood, obtainable from a fresh human venous whole blood sample of 1 ml volume, which is heated in a cylindrical polyethylene container with 3 mm inner diameter and 3.4 mm outer diameter for about 0.5 min. to about 10 min. at a temperature of about between 70° C. and 100° C. and/or
(vii) said level of denaturation is defined by the change of red-colored hemoglobin to brown as an indicator, wherein $Fe^{2+}$ is reduced to $Fe^{3+}$ in the hemoglobin complex to a degree of at least 80%, preferably 90% and even more preferably 95%.

The inventor found that a stabilizing matrix needs physical properties, which are a high viscosity. The viscosity of the matrix can be measured using a ball test, wherein the foam is prepared in a 10 ml syringe, the syringe placed in a 60° angle from horizontal inclined position. A small round ball of 13 mm diameter and 1.3 g in weight is placed on top of the foam and velocity of the ball moving through the foam is measured. Using this setting, the velocity of the ball is 1.7-2.3 cm/s in common microfoams.

In a preferred embodiment of the invention the foam slows the ball to a velocity of less than 1 cm/s, preferably less than 0.7 cm/s, more preferably less than 0.5 cm/s, most preferably less than 0.25 cm/s.

The term "matrix" defines a structure which serves as a physical carrier. This does not exclude few chemical bindings, but the main effect is physical. To avoid or reduce chemical bindings of the sclerosant agents, these are preferably added after appropriate generation of the matrix.

It is preferable that the foam comprising the matrix has a longer half-life in vitro than common sclerosant foams, while still being biologically degradable. Preferably the foam comprising the matrix has a half-life of at least 30 minutes or longer, more preferably at least one hour or longer, even more preferably at least two hours, more preferably at least four hours, most preferably at least six hours.

In a preferred embodiment of the invention the foam comprising the matrix is stable inside a vein for at least 4 hours, meaning after 4 hours the foam is still visible in ultrasound imaging.

In a preferred embodiment of the invention the matrix is a composition, which has physical properties comparable a blood sample of 1 ml kept in a cylindrical polyethylene container with 3 mm inner diameter and 3.4 mm outer diameter is denatured by conducted heat for 0.2 to 10 minutes at between 50 to 100° C., more preferably 0.4 to 7.5 minutes at 60 to 100° C. and most preferably for 0.5-7 minutes at 75-100° C., referring to the heating temperature at the outer margin of the blood sample container.

In a preferred embodiment the matrix has physical properties comparable to denatured blood, which corresponds to a whole blood sample of 1 ml volume in a cylindrical polyethylene container with 3 mm inner diameter and 3.4 mm outer diameter, heated by circumferential contact to a heating element for 3 min. at 81° C.

In preferred embodiments the matrix is a biocompatible composition. More preferably the matrix is a biocompatible, pharmaceutically acceptable composition.

Suitable matrix compositions are known to the person skilled in the art. In preferred embodiments the matrix comprises various biodegradable polymers-PCL, PLA and PLGA alone or in combination. Alternatively cross linked hyaluronic acid and/or a mixture of denatured human proteins, e.g. denatured human serum albumin or synthetic similar proteins might be used.

Figure 3C:
Figure 4A:
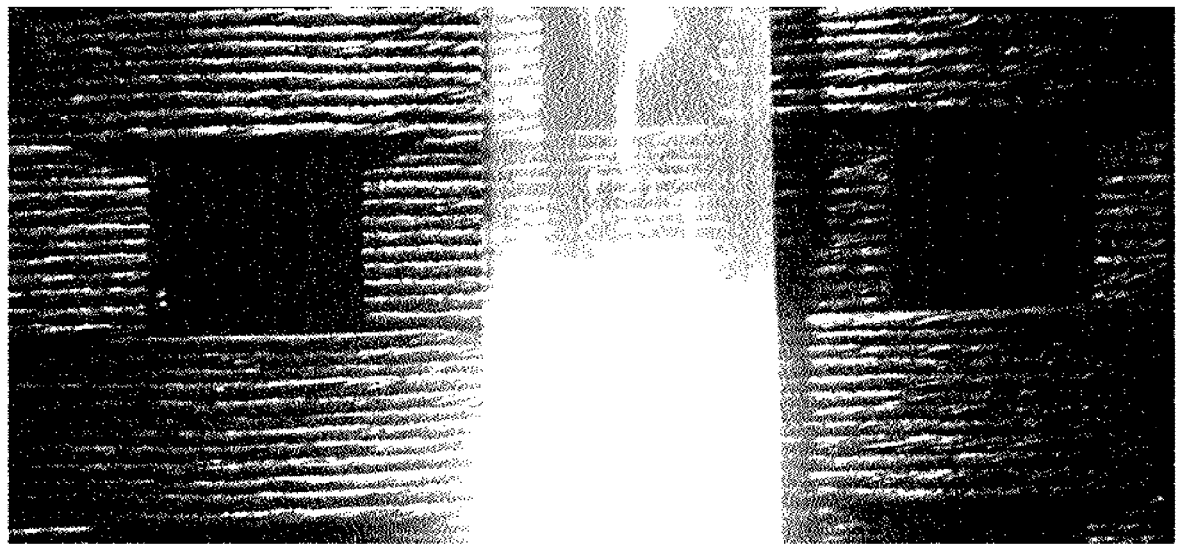
Figure 4B:
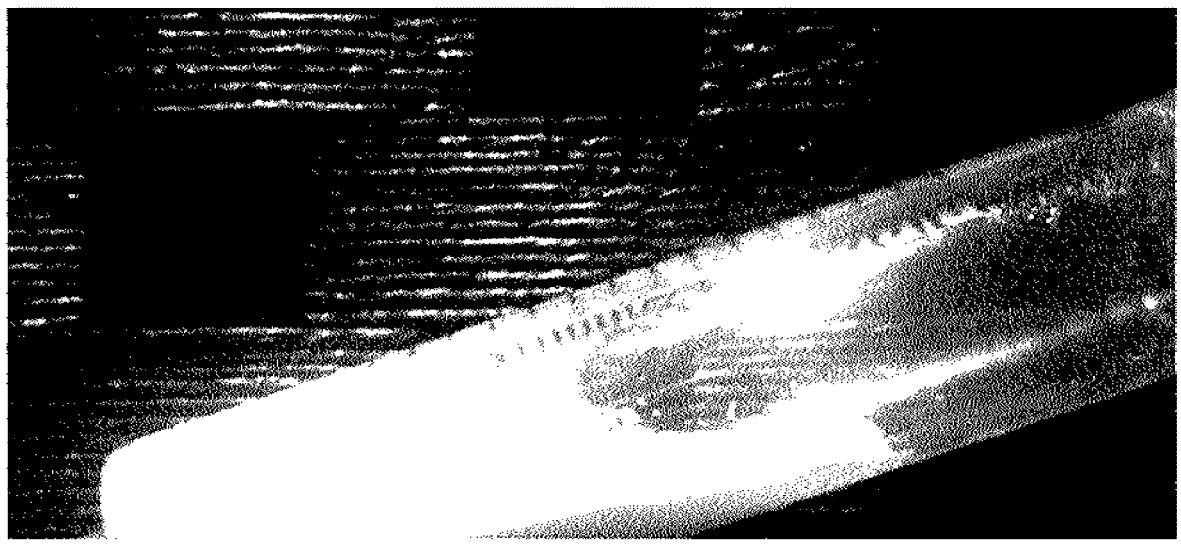
Figure 4C:
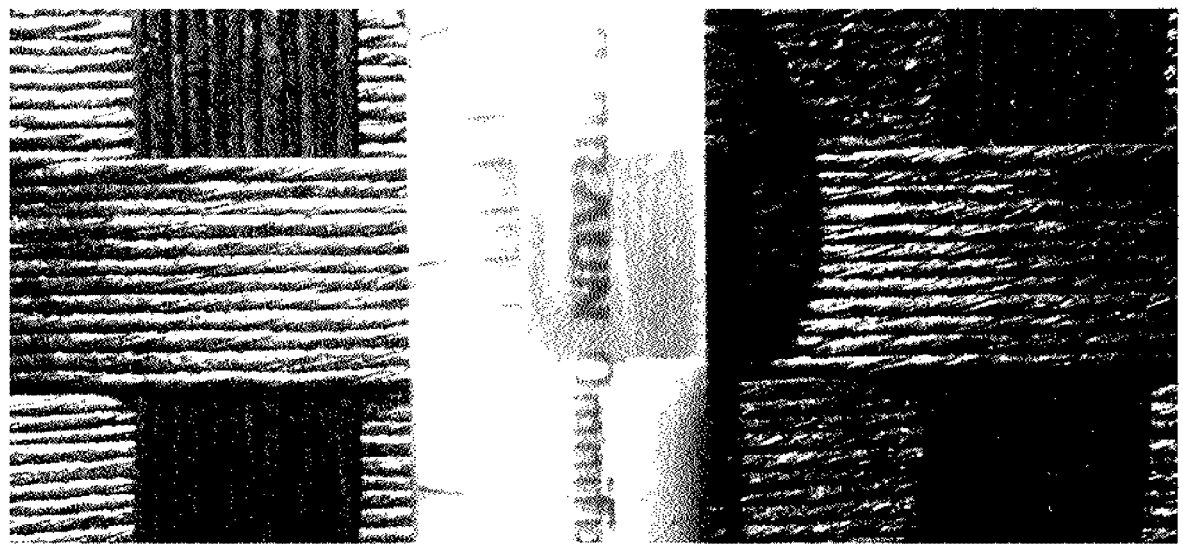
Figure 4D:
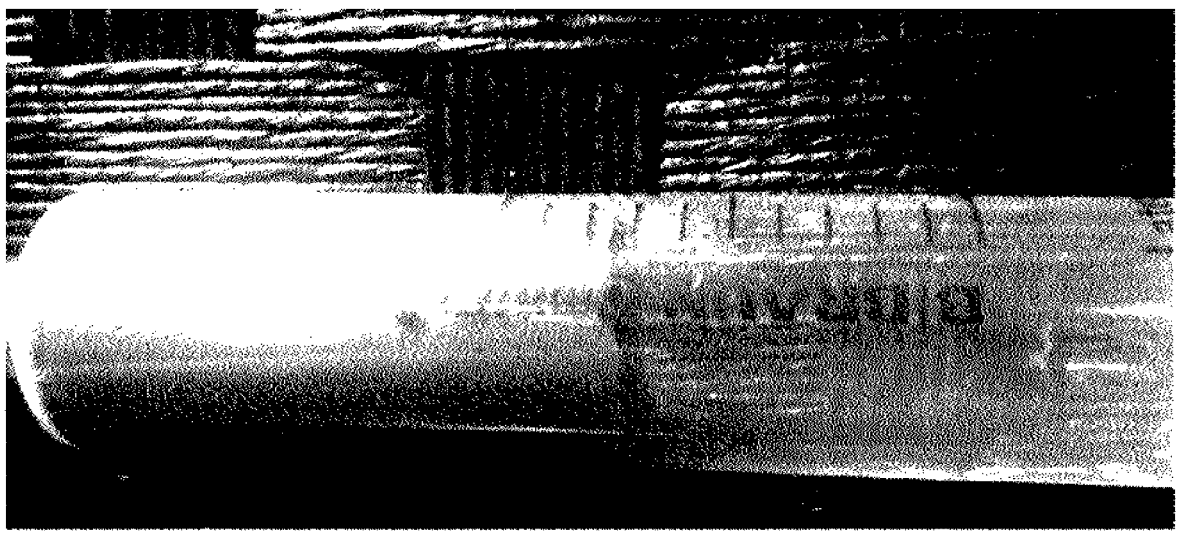

The inventor unexpectedly found that a dispersion of denatured human blood can be used as a carrier for foaming liquid sclerosant chemicals with all the desired features and properties. The inventor found that sclerosant drug foams comprising denatured blood of the patient's own blood show stunningly improved properties. In particular, the sclerosant drug foam according to the present invention has a half live of 2 h to 14 days which increases the time of contact between the sclerosant drug and the target structures (FIG. 3). Thereby, efficiency of the sclerotherapy is unexpectedly increased. The foam according to the present invention shows a tremendously higher stiffness than sclerosant foams of prior art (FIG. 3). Stiffness and density can be adjusted by the ratio of blood, liquid, sclerosant agent and gas. In contrary to the disadvantageous sound shadows of common foams (FIG. 1) the ultrasound appearance of the blood matrix based foam varies from neglectable acoustic shadow to no shadow at all (FIG. 2). The application is more precise (FIG. 4), restricting the effect to the diseased target vein and preserve healthy veins. The spasm period is much longer, as spasm depends on the presence of the sclerosant agent, which is longer held in place by the blood-based matrix. The distribution of chemicals to the circulation is much slower and therefore side effects even rarer than in conventional sclerosant foams. The target vein occlusion occurs much faster and with a smaller final lumen, supporting a short and symptom free healing period.

The patient's own blood seems to be the most natural and the safest source of particles to produce sclerosant foam with improved properties. As denaturation leaves the primary structure of blood proteins unchanged, adverse reactions due to the matrix are not to be expected.

Although blood samples could be processed in a laboratory, the aim of the invention is to provide a closed system where a sterile foam is produced in a system attached to the catheter and injected without any contact to the environment. Technology even allows miniaturization to install the system totally inside of a catheter, or systems working within a catheter extension.

The invention further relates to a particular injectable sclerosant drug foam comprising:
(i) denatured blood;
(ii) at least one fluid;
(iii) at least one sclerosant drug;
(iv) a medical gas or medical gas mixture acceptable for intravenous use, (v) wherein the denatured blood is characterized by a certain level of denaturation, (vi) wherein said level of denaturation is defined by the color of the denatured blood and said color of denatured blood is comparable to or identical to blood being denatured as follows:

A fresh human venous whole blood sample of 1 ml volume is heated in a cylindrical polyethylene container with 3 mm inner diameter and 3.4 mm outer diameter for about 0.5 min. to about 10 min. at a temperature of about between 70° C. and 100° C. and/or (vii) said level of denaturation is defined by the change of red-colored hemoglobin to brown as an indicator, wherein $Fe^{2+}$ is reduced to $Fe^{3+}$ in the hemoglobin complex to a degree of at least 80%, preferably 90% and even more preferably 95%.

For the purpose of the present invention the term blood refers to human venous whole blood. Preferably the blood is whole blood of the patient.

In the present invention the expression "denatured blood" is frequently used. For several purposes, it may be adequate to keep certain proteins vital, like those for coagulation. On the other hand, calling the procedure "partial denaturing" would not express that a majority of the proteins has to be denatured. The desired degree of denaturation in the sense of the invention is defined as preferably exceeding 90% of the contained blood proteins and blood cell proteins.

Blood denaturation may be performed by heat, in particular conducted heat. Blood may also be denatured by radiation, such as microwave, radiofrequency, infrared or other kinds of electromagnetic radiation, or by chemical means including enzymes. Depending on the kind of denaturation, different arrays may be required for a device producing blood-based sclerofoam (FIG. 5 a-c), and all features shown in those arrays may be combined.

The term "matrix" defines a structure which serves as a physical carrier. This does not exclude few chemical bindings, but the main effect is physical. To avoid or reduce chemical bindings of the sclerosant agents, these are always added after appropriate denaturation of the blood sample.

In a preferred embodiment of the invention a blood sample of 1 ml kept in a cylindrical polyethylene container with 3 mm inner diameter and 3.4 mm outer diameter is denatured by conducted heat for 0.2 to 10 minutes at between 50 to 100° C., more preferably 0.4 to 7.5 minutes at 60 to 100° C. and most preferably for 0.5-7 minutes at 75-100° C., referring to the heating temperature at the outer margin of the blood sample container.

The term denaturation means the process of irreversible changes in the natural 3-dimensional structure of proteins. In heat denaturation not only heating temperature and exposure time will determine the result, but the distribution of temperatures within the sample over time. Due to geometric factors any heating process will create different temperatures in a sample at a given time, comparable to the boiling of an egg. Therefore, the required sample temperature can only be given with a tolerance of 5-10% as it is rarely uniform throughout the sample.

Heat denaturation starts at about 50° C. with dissolving of the internal hydrogen bonds, proteins unfold and lose their biological function. This correlates with the inactivation of most of the vital enzymes.

In the range of 60-65° C. hemoglobin will change to methemoglobin by iron oxidation, predominantly responsible for a change in color from red to brown. At the same time, haemolysis and coagulation occur. Membrane lipids will melt and cell structures disintegrate. Above 70° C. also disulfide bridges will dissolve, which form the intermolecular connections. In consequence the shape of spherical proteins will change to filiform. Blood serum will form a solid gel starting at 72° C. Above 80° C. proteins will even lose their secondary structure. However, the primary structure is maintained and there is no change in the chemical composition.

The inventor observed two signs indicating the desired degree of denaturation of 2 ml human whole blood samples in glass test-tubes of 1.8 cm diameter, heated in a water bath of 60-80° C. will change their color from red to brown within 4-18 minutes. It could be shown that this color change correlates to the quality of the foam produced, according to its half-life. Therefore, the color change was adapted as a major criterion for producing a foam according to the invention. Using smaller tubes, the required time to denaturation was much shorter (Tab. 1 a-b).

Temperatures of above 100° C. may further accelerate blood denaturation, and such procedures are feasible when increased pressure is tolerated by the device.

In a preferred embodiment the denatured blood corresponds to a whole blood sample of 1 ml volume in a cylindrical polyethylene container with 3 mm inner diameter and 3.4 mm outer diameter, heated by circumferential contact to a heating element for 3 min. at 81° C.

The color of the blood changes with the degree of denaturing. Non-denatured, native, oxygenated blood exhibits a bright red color. Deoxygenated blood, e.g. from veins, has a darker shade of red. Denaturing or partially denaturing of the blood triggers a change of the color of the blood. Denatured blood in the context of the present exhibits a dark brown color.

Table 3 a, b: These tables show the time required to obtain a color change from red to brown, depending on the size of the sample and the surrounding temperature. For medical purpose, all the sample volume has to be denatured. Therefore, the color was measured by a colorimeter within the center of the probe.

TABLE 3a color change from red to brown in a sample measuring r = 1.9 mm and length = 80 mm

| | Temperature in ° C. | | | | | | |
|---|---|---|---|---|---|---|---|
| | 60 | 65 | 70 | 75 | 80 | 85 | 90 | 95 |
| time | — | — | 6 | 4 | 3 | 2 | 1 | 0.5 |

TABLE 3b color change from red to brown in a sample measuring r = 7.0 mm, length = 2.5 mm

| | Temperature in ° C. | | | | | | |
|---|---|---|---|---|---|---|---|
| | 60 | 65 | 70 | 75 | 80 | 85 | 90 | 95 |
| time | — | — | 12 | 10 | 8 | 6 | 4 | 2 |

As color impressions may depend on the investigator's eye it is important to define "red" and "brown". Although there is a wide color range depending of the degree of oxygenation, nutrition factors and maybe medication, "red" can be defined in several ways. One way is in comparison to standardized colors, like the German RAL color number system. Another way is according to RGB values, which is often used in colorimetric measurements. In the context of the invention, "red" is defined as being RAL 3003, or RGB 184-26-14, while RAL 3004 is indefinite, equivalent to RGB 109-29-20. RAL 3003 is "brown", equivalent to RGB 141-26-33. Other "brown" colors observable in denaturized blood samples according to the invention are e.g. RAL 3005-3011, 8007-8017 and 8023-8025. Other "red" colors of native or not sufficiently denaturized blood samples are represented by e.g. RAL color numbers 3000-3003, 3013, 3016, and 3027.

As a more precise alternative, "brown" in the sense of the invention can be defined as a state where more than 80%, preferably more than 90% and even more preferably more than 95% of the iron has turned from $Fe^{2+}$ to $Fe^{3+}$. This classification is based on laboratory tests and is not suitable for an immediate use in clinical application, but can be used for calibration. The amount of oxidized iron could be determined using oximetry.

Figure 6:
Figure 7A:
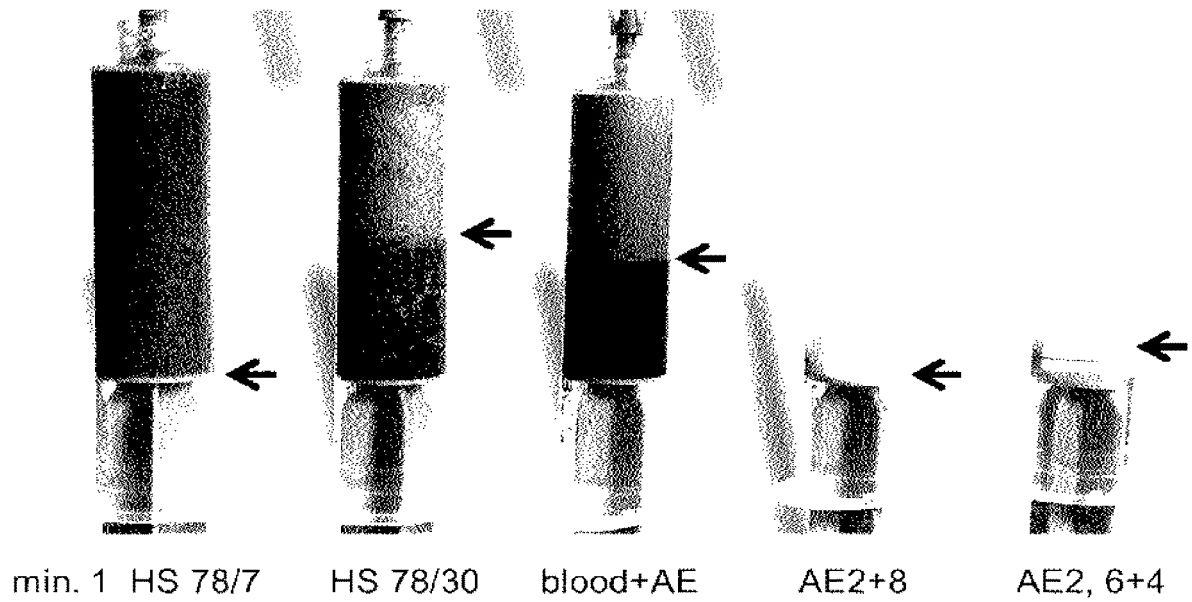
Figure 7B:
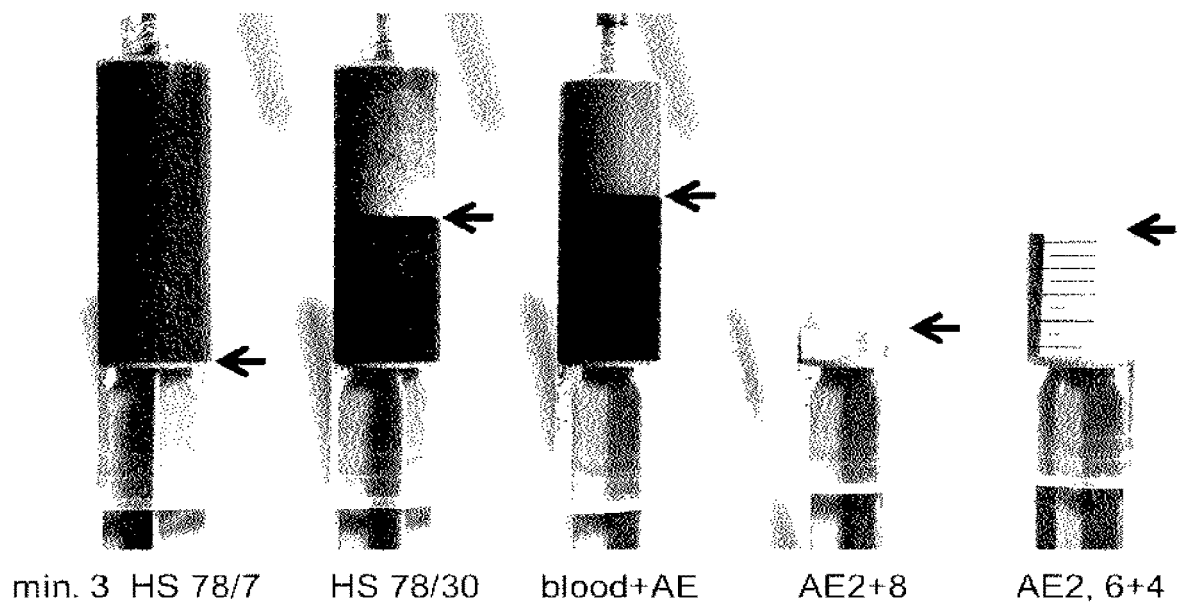
Figure 7C:
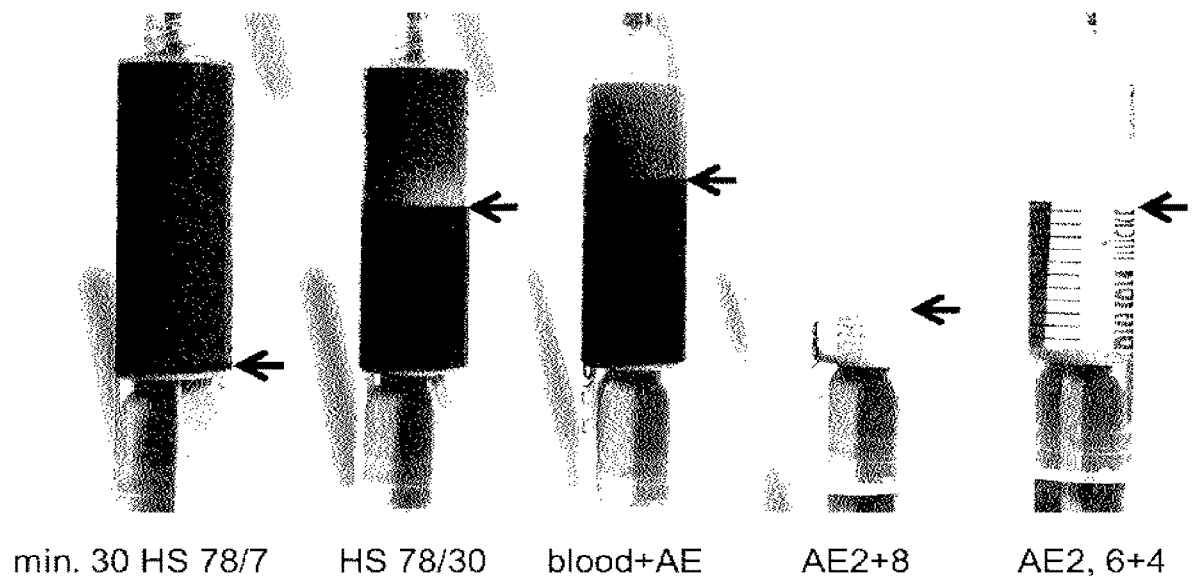
Figure 7D:
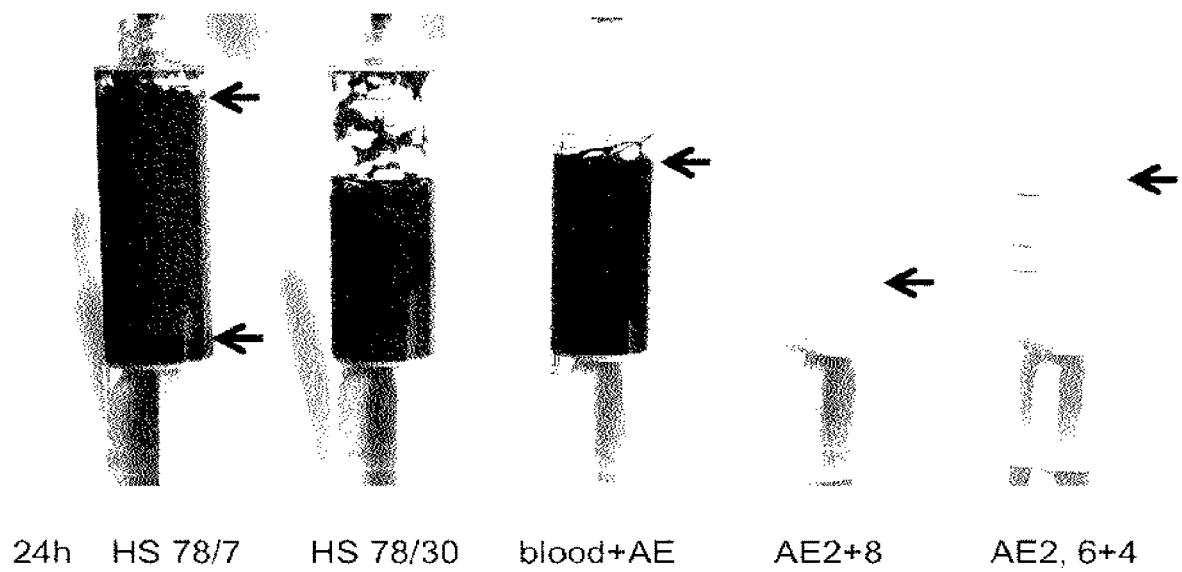

One further feature of a heat-treated blood sample suitable for producing a carrier for sclerosant media is the firmness of the substance due to denaturation and coagulation. If blood denatured according to the invention is spread from a syringe to a tissue, it appears as a stable body which does not visibly change its shape as far as no external forces are applied (FIG. 6). This feature also may be used to define appropriate denaturation.

The following explanations relate to both, the sclerosant drug foam comprising a matrix and the particular embodiment comprising denatured blood.

In most embodiments the at least one fluid is a pharmaceutically acceptable liquid, which is used to disperse the denatured blood.

In some embodiments of the invention the denatured blood is dispersed with a pharmaceutically acceptable liquid, which are preferably destilled water purified for injection purpose, or a sterile isotonic sodium chloride solution. In a preferred embodiment of the invention the pharmaceutically acceptable liquid also comprises the sclerosant drug in dissolved or suspended form. In a more preferred embodiment the pharmaceutically acceptable liquid is the sclerosant drug.

A sclerosant drug in context of the method for production of a sclerosant drug foam may be any substance which is suited for sclerotherapy, i.e. which changes the protein structures of vein endothelium in the sense of a permanent denaturation within a few seconds of contact. In a preferred embodiment the sclerosant drug according to the invention is selected from the group consisting of alcohols with detergent properties such as, polidocanol or sodium tetradecyl sulphate. Different dilutions of the drugs are available commercially. For polidocanol solutions with concentrations ranging from 0.25% to 4% in suited solvents (e.g. ethanol) are available (e.g. Aethoxysklerol, Kreussler Pharma, Germany). Thus, in a preferred embodiment the sclerosant drug is a solution of 0.1% to 10% polidocanol in a suited solvent, preferably 0.2% to 7%, even more preferably 0.25% to 4% polidocanol in a suited solvent. The most preferred concentration is between 1% and 3%.

To produce sclerosant foams according to the invention, the dispersion of denatured blood is mixed with a medical gas or gas mixture acceptable for intravenous use. Such gases are $N_2$, $O_2$ and $CO_2$, and even filtrated room air is appropriate for foam preparation with recommended maximal injection of 8 ml.

For use in the treatment of insufficient veins, for a 10 ml quantity of injectable sclerosant foam compositions of 1-4 ml denatured blood, 2-6 ml of disperging fluid and 2-6 ml of medical gas is suggested, while higher quantities of denatured blood will produce higher viscosities with potential advantages for use in short-distance targets and higher quantities of fluid and gas will produce foams of lesser viscosities suitable to reach locations even at above 10 cm distance from the catheter outlet.

It is clear to the person skilled in the art that a sclerosant drug foam for use as a medicament has to be prepared immediately before use.

Methods of foaming are known by those skilled in the art. One way is to mix the dispersion containing the matrix and/or preferably denatured blood, at least one liquid and at least one sclerosant drug with a gas or a gas mixture and obtain a foam when specific forces are reached. Any of the known methods to prepare sclerosant foams will be applicable. Another way to prepare foam based on a matrix preferably of denatured blood is to use gas or steam already during the step of generating the matrix by obtaining a primary foam, and then add a liquid sclerosant medium and conclude with a final mixing and foaming.

The inventor found it desirable to fragmentize the matrix or the denatured human blood or fractions thereof to particles below monocyte size (120 μm) in order to circumvent the danger of embolism or damages in other organs. The procedural aim of particle size is 5-300 μm, preferably 5-120 μm, even more preferably 5-50 μm. The foam bubble size is 10-300 μm, preferably 20-200 μm, even more preferably 30-120 μm.

Particle size can be minimized by increasing the forces applied to the dispersion, or by including cutting means. Similarly, bubble size can be minimized by increasing the forces applied during foaming.

In another embodiment of the invention the particle size is reduced by use of a chopping element. A preferred chopping element for use in this invention comprises: at least one cutting edge, preferably several cutting edges located within a connecting tube structure, wherein the cutting edges are arranged to face the particle inflow and cover less than 10% of the tube cross-section area. Preferably, the flow of particle-containing fluid or dispersion is accelerated before hitting the chopping element.

A "cutting edge" in context of the present invention is an edge, which is suited to chop particulates of partially denatured blood when applying a force on the particulates with said edge. The two cutting edges may be connected, i.e. they are formed by one cutting means. Thus, in one embodiment of the present invention the at least two cutting edges are formed by one double edged cutting means. In a further embodiment each of the at least two cutting edges is formed by a separate cutting means.

By "cutting means" in context of the present invention are means comprising at least one cutting edge. The material of cutting means may be selected by those skilled in the art. The skilled person will unambiguously recognize that the material, however, has to provide a certain degree of rigidity to allow the cutting edge(s) to chop particulates of partially denatured blood. In one embodiment the cutting means consists of a material selected from the group consisting of metal, steel, plastic, glass, ceramic or the like. In one embodiment the cutting means is a double edged blade. In a further embodiment the cutting means is one double edged cutting wire.

Mechanical forces are required for the transport of blood, fluids, dispersion, gas and foam within the system, and in particular for disperging, filtering and foaming. In a preferred embodiment, mechanical forces are generated by external pressure. This may include positive and negative pressure, or alternating pressures. Pressures can be obtained by pneumatic or hydraulic elements, but also by electromechanic elements. Another means to execute forces is by rotational device like propellers, which are usually electricity driven.

While the parts transferring energy to denatured blood, fluids or the dispersion (FIG. 5) are mandatory elements of the device, the source of the applied energy may be external, e.g. as rotational motor or pressure device, and the energy is transmitted via particular connectors.

A dispersion is a system in which particles are dispersed in a continuous phase of a different composition or state, and the expression is less precise than "suspension" and "emulsion", which may both be involved when dealing with blood. In the present case a dispersion is created from denatured blood and at least one fluid like isotonic saline. While blood denatured by conducted heat forms a kind of a solid body, other modi of denaturation like chemicals or mixing with heated fluids or gases will not form solid bodies. Therefore, the term "dispersion" was chosen to characterize a mixture of small solid or fluid particles within another fluid, with no visible precipitation during the phase until it is transferred to a foam by mixing with gas.

To obtain a determined maximum particle size with the aim to minimize the risk of microembolism, in a preferred embodiment the sclerosant drug foam is filtered during production. In a preferred embodiment of the invention this filtration step removes all particles exceeding a size of greater than 120 µm. This equals the size of the biggest natural blood cells.

In a foam according to the invention, the denatured blood content is 10-50% of the foam volume. As there are recommendations of a recent Consensus Conference concerning limiting the amount of common sclerosant foam per session to 10 ml, a similar recommendation may be derived also for the sclerosant foam according to the invention. As about 44% of whole blood volume is cellular, and percentage of denatured blood in the foam is 10-50%, the maximum amount of denatured blood cells is 2.2 ml. All blood cell remnants from the foam can be disintegrated by natural pathways, like the body does with aged blood cells at a much higher rate day by day. Much larger amounts of blood are left in veins treated by sclerotherapy or thermo-occlusive methods for metabolism and transformation. The foam according to the present invention, compared to sclerofoams of prior kind, contains up to 50% less gas which is favourable as gas amounts are suspected to be responsible for side effects of foam therapy like impaired vision or bronchospasms.

Sometimes, it may be useful to remove parts of the whole blood or concentrate others, e.g. erythrocytes may be reduced to reduce the color intensity, and fatty remnants may be advisable to remove from the denaturized blood in patients with elevated blood lipids. Leukocytes may be removed when fearing pyrogenetic mediator discharge, and vital thrombocytes may be concentrated to increase the coagulation process within the target vessel. For this reason, besides the whole blood addressed in the descriptions of the invention, the option to instead use fractions of blood is always included. Those skilled in the art know the required procedures of cell elimination or concentration by filtration, hydro-extraction and others.

In particular, for use in sclerotherapy it may be desirable that the sclerosant drug foam according to the present invention comprises active platelets, i.e. adhesive platelets that can activate local clotting. Thus, it would be necessary to inactivate the inhibitory proteins and enzymes while maintaining a sufficient amount of active platelets. The degree of denaturing can be selected by those skilled in the art. In a preferred embodiment essentially all proteins and enzymes inhibiting the sclerosant drug are inactivated in the partially denatured blood. The skilled artisan knows methods to determine the degree of denaturing of the blood. For example the activity of different enzymes within the partially denatured blood may be compared to the activity of the respective enzymes in non-denatured blood. Such "indicator" enzymes are well known in the art. One indicator enzyme is catalase. Thus, the degree of denaturing of the blood can be tested by the catalase test. The presence of catalase enzyme in the test isolate is detected using hydrogen peroxide. If blood or partially denatured blood possess catalase (i.e., is catalase-positive), bubbles of oxygen are observed when blood or partially denatured blood is added to hydrogen peroxide. The test is done by placing a drop of hydrogen peroxide on a microscope slide. An applicator stick is contacted with blood or partially denatured and then applied into the hydrogen peroxide drop. In one embodiment no bubbles of oxygen are observed when partially denatured blood is applied into a hydrogen peroxide drop.

The sclerosant drug foam according to the invention is for use as a medicament, in particular as a medicament in sclerotherapy.

The method to produce a sclerosant drug foam according to the invention comprises the steps of providing denatured blood or denature blood fractions, dispersing the denatured blood at a temperature of 10-85° C. with a pharmaceutically acceptable liquid wherein preferably the pharmaceutically acceptable liquid is or comprises said at least one sclerosant drug, or mixing the dispersion with said at least one sclerosant drug, finally foaming the dispersion with medical a gas suitable for intravenous use, like $O_2$, $CO_2$ or mixtures thereof (FIG. 5 a-c). The use of higher temperatures than 85° C. is possible but may interfere with the evaporation temperature of alcohols or other sclerosant media unless system pressure is increased. Also lower temperatures than 10° C. may be used for added fluids, if the purpose is rapid cooling. The produced sclerofoam should be at a temperature of 10-85° C., preferably 15-40° C., even more preferably 20-37° C. Foam temperatures of above 37° C. may contribute to an increased denaturing effect on the endothelium but bear the risk of unwanted thermal damage, e.g. in structures near to the skin.

The basic device to produce sclerosant drug foam according to the invention (FIG. 5a) comprises a catheter for blood sampling and foam distribution (1), a first container (4) for blood collection and denaturation, an external element for denaturation by heat, radiation or chemicals (6) to be physically or thermally connected to the first container, a second container (10) for at least one fluid and/or at least one sclerosant agent, a unit (7a) to apply mechanical force to the contents of the first and/or second container for mixing/dispersing, optionally a chopping element (7b), optionally a filter element (13), a third container to hold the dispersion (14), a fourth container containing a medical gas (18), a unit (16) to apply mechanical force to the contents of the third and/or fourth container for foaming, two-way switches, one-way valves, single stop cocks or combinations thereof (2, 3, 9, 15, 17) to selectively connect the containers and units, auxiliary access to the device, e.g. to apply negative or positive pressure, or to supply fluids or gases for foam production or for rinsing (4a, 8, 11a, 11b, 19), and connection elements connecting all modular parts.

In the procedure, an amount of blood is taken from the target vein through the catheter (1) and guided to the first container (4) where the blood is denatured by help of the denaturation unit (6). The denatured blood is mixed with a fluid and/or a sclerosant agent from a second container (10) to form a dispersion by application of mechanical forces (7). If the mixing procedure alone would leave particles above 120 µm, a chopping unit (7b) is added and the dispersion passed once or several times. To ensure no particles above 120 µm are present in the dispersion, it may be filtered (13) and guided to a third container (14). Then a connection to a fourth container (18) providing a medical gas is established and a foam produced by mixing the gas with the dispersion by applying mechanical force (16). The foam is finally provided in one of the containers (14, 18) and transferred to the diseased vein via catheter (1).

In another embodiment, the procedure comprises the steps of denaturing blood by introduction of a pharmaceutically acceptable liquid heated to 78-100° C. into the blood containing compartment of the device, or by introduction of steams of such liquids of 80-130° C. wherein the liquid may be or may contain at least one sclerosant, or by introduction of heated gas suitable for intravenous use like $O_2$ and/or $CO_2$, or by combination of these means. After cooling to below 77° C. and adding at least one sclerosant drug, further dispersing of the mixture is performed until sufficient small particle size is obtained, and further foaming of the dispersion with present or added gas suitable for intravenous use, like $O_2$ and/or $CO_2$ until the desired bubble size is obtained. This embodiment produces the required dispersion without requiring high mechanical forces as there is no solid denatured blood to be dissolved (FIG. 5b). The indicator of color change applies to this method, but the indicator of change in viscosity does not apply as no solid body is formed during blood denaturation.

In this embodiment, a device for the production of a sclerosant drug foam minimizing mechanical forces for mixing and disperging is described (FIG. 5b), comprising a catheter for blood sampling and foam distribution (1), a first container (4) for blood collection and denaturation by heated fluid, an element for supply with heated fluid (6), a second container (10) for at least one sclerosant agent, a unit (16) to apply mechanical force to the contents of the first and/or second container for foaming after adding medical gas, an access to add sclerosant or a medical gas (8), or to apply negative or positive pressure or for rinsing (11a, 11b); two-way switches, three-way switches, one-way valves, single stop cocks or combinations thereof (2, 3a, 3b, 9) and connection elements connecting all modular parts.

For the foam producing procedure, an amount of blood is taken from the target vein through the catheter (1) and guided to the first container (4) where the blood is denatured by help of the denaturation unit (5), in this particular embodiment by mixing with a heated fluid, e.g. isotonic saline or aqua destillata of 80-100° C., then adding at least one sclerosant agent from a second container (10) to form a dispersion, finally adding a medical gas is added via auxiliary port (8) and foaming performed by mechanical force (16) or pressure variations or for rinsing (11a, 11b). The resulting foam is transferred to the diseased vein via catheter (1).

In another embodiment, a simplified device for the production of a sclerosant drug foam (FIG. 5c) is described, comprising a catheter for blood sampling and foam distribution (1), a first container (4) for blood collection and denaturation (5), elements for denaturation by heat or radiation (5) or chemicals (4a), a second container (10) for at least one fluid and/or at least one sclerosant agent, a unit (7) to apply mechanical force to the contents of the first and/or second container for mixing/dispersing and foaming after adding medical gas, an access to add a medical gas (16), two-way switches, one-way valves or single stop cocks or combinations thereof (2,3), auxiliary access to the device, e.g. to apply negative or positive pressure or for rinsing (11a, 11b) and connection elements connecting all modular parts.

For the production of blood-based sclerosant foam, an amount of blood is taken from the target vein through the catheter (1) and guided to the first container (4) where the blood is denatured by help of the denaturation unit (5). The denatured blood is mixed with a fluid and a sclerosant agent from a second container (10) to form a dispersion by application of mechanical forces (7). A medical gas is added via auxiliary port (8) and foaming performed by mechanical force (7). The foam is finally collected in one of the containers (4, 10) and transferred to the diseased vein via catheter (1).

In all embodiments, the components except the catheter to the target vein may be miniaturized to fit into the catheter or into a catheter extension with an outer diameter of below 30 mm, preferably below 20 mm, even more preferably below 10 mm.

The device construction, in particular concerning the containers, may be modular or integral. In a preferred embodiment, the units for heating/denaturation (6), dispersing (7) and foaming (16) are modular.

The containers, connectors, switches and elements for filtering, chopping and foaming may be provided as single parts to be assembled by the user under sterile conditions prior to use, however preferably all parts are provided completely assembled and sterilized as a one-way system, except the external unit for physical denaturation. The switches may be common one-way, two-way or three-way cocks for manual handling, they may also be electric, magnetic or electromagnetic, or pressure operated.

The invention further relates to a kit for the production a sclerosant drug foam comprising a unit for blood denaturing and dispersing, optionally at least one fluid, optionally at least one sclerosant drug, at least one medical gas, and optionally one or several catheters for venous access and foam deployment.

The present invention also relates to a treatment of venous insufficiency the method comprising the steps of:
(i) establishing an access to one or several target veins, preferably to the largest target vein, by use of canulas, microcatheters or preferably by catheters, and taking of at least one autologous blood sample of 0.5-4 ml;
(ii) preparing a sclerosant drug foam by mixing at least one sclerosant medium with a matrix of disperged denatured blood;
(ii) injecting the sclerosant drug foam into the target veins preferably using ultrasound monitoring;
(iii) removal of intravenous foam conducting elements.

Like outlined previously, the use of catheters is preferred, as foam deployment is more precise and more efficient when large-lumen device is used for injection because for physical reasons blood replacement in veins by foam is more effective.

The venous access is established by puncture under local anaesthesia. In short or very tortuous diseased vein segments usual peripheral venous access systems of 0.8-2.2 mm diameter and 40-60 mm in length may be used for antegrade or retrograde foam injection. They consist of a cannula covered by a plastic tube except for the tip and allow direct vein access, where the cannula is withdrawn and the tube remains within the vein for a time according to its purpose. However, similar microcatheter products with included cannula of 80-200 mm in length and the option to deploy the foam during withdrawal of the catheter are preferred. For very large and long diseased veins like saphenous veins (e.g. vena saphena magna et parva) it is preferred to work with catheters of 1.2-2.8 mm in diameter, 40-80 cm in length and provided with non-stick properties and one or several optional sideholes. These catheters are introduced in SELDINGER technique using a guide wire, or as stand-alone procedure using an implemented cannula.

The sclerosant drug foam, as meant for use in humans, is generally produced under sterile conditions. Concepts of producing blood-based sclerosant foam which operate in a closed system are preferred, limiting the contact to the environment to the supply of liquids, sclerosant and medical gases under sterile conditions. This also excludes the risk of blood contamination or sample confusion. Preferably the device is provided sterile, or can be sterilized.

In one embodiment the sclerosant drug foam is prepared in a device within or a device connected to a catheter. Ideally, the sclerosant drug foam is dispersed in the pharmaceutically acceptable liquid using mechanical force, e.g. using a chopping element.

The invention also relates to a method for the production of a sclerosant drug foam comprising the steps of:
(a) denaturing blood by introduction of a pharmaceutically acceptable liquid heated to 78-100° C. into the blood containing compartment of A device, or by the introduction of steam of between 80 and 130° C. wherein the liquid may be or may contain at least one sclerosant, or by introduction of heated gas suitable for intravenous use like $O_2$ and/or $CO_2$, or by combination of these means;
(b) cooling to below 77° C. and add at least one sclerosant drug if not included in step (a);
(c) further dispersing of the mixture generated in steps (a)-(b) until the maximum particle size as defined above is reached,
(e) further foaming of the dispersion with present or added gas suitable for intravenous use, like $O_2$ and/or $CO_2$, if mean bubble size is above 120 μm.

The invention relates to various device types.

In one embodiment the device for the production of a sclerosant drug foam minimizing mechanical forces for mixing and dispersing, comprises:
(a)0 a catheter for blood sampling and foam distribution (1),
(b) a first container (4) for blood collection and denaturation,
(c) an element for supplying the heated fluid (6),
(d) a second container (10) for at least one sclerosant agent,
(e) a unit (16) for applying mechanical force to the contents of the first and/or second container for foaming after adding medical gas,
(f) optionally access to add sclerosant or a medical gas (8), or to apply negative or positive pressure, or for rinsing (11a, 11b).
(j) optionally two-way switches, three-way switches, one-way valves, single stop cocks or combinations thereof (2, 3a, 3b, 9)
(k) connection elements connecting all modular parts, Here, an amount of blood is taken from the target vein through the catheter (1) and guided to the first container (4) where the blood is denatured by help of the denaturation unit (5), in this particular embodiment by mixing with a heated fluid, e.g. isotonic saline or distilled water of 80° C. to 100° C., then adding at least one sclerosant agent from a second container (10) to form a dispersion, finally adding a medical gas is added via auxiliary port (8) and foaming performed by mechanical force (16) or pressure variations (8, 11, 4a). The resulting foam is transferred to the diseased vein via catheter (1).

The invention also relates to a device for the production of a sclerosant drug foam comprising:
(a) a catheter for blood sampling and foam distribution (1),
(b) first container (4) for blood collection and denaturation (5),
(c) one or more elements for denaturation by heat or radiation (5) or chemicals (4a),
(d) a second container (10) for at least one fluid and/or at least one sclerosant agent,
(e) a unit (7) to apply mechanical force to the contents of the first and/or second container for mixing/dispersing and foaming after adding medical gas,
(f) means for adding a medical gas (16),
(j) optionally two-way switches, one-way valves or single stop cocks or combinations thereof (2,3)
(k) optionally auxiliary means for applying negative or positive pressure, or for rinsing (11a, 11b)
(l) connection elements connecting all modular parts, Here, an amount of blood is taken from the target vein through the catheter (1) and guided to the first container (4) where the blood is denatured by help of the denaturation unit (5). The denatured blood is mixed with a fluid and a sclerosant agent from a second container (10) to form a dispersion by application of mechanical forces (7). A medical gas is added via auxiliary port (16) and foaming performed by mechanical force (7). The foam is finally collected in one of the containers (4, 10) and transferred to the diseased vein via catheter (1).

Preferably, some or all components are miniaturized to fit into the catheter or into a catheter extension with an outer diameter of below 30 mm, preferably below 20 mm, even more preferably below 10 mm.

Preferably, the device is modular.

Preferably, the device is integral, including or excluding the heating/denaturation unit (6).

Preferably the one or more of the containers are a syringe.

The invention relates also to a method of treating venous insufficiency using a sclerosant drug foam comprising the steps of
(i) establishing an access to one or several target veins, preferably to the largest target vein, by use of canulas, microcatheters or preferably catheters, and taking of at least one autologous blood sample;
(ii) preparing a sclerosant drug foam as defined above;
(ii) injecting the sclerosant drug foam into the target veins preferably using ultrasound monitoring;
(iii) removing the intravenous foam conducting elements (catheter).

EXAMPLES

Comparison of Regular Sclerosant Foam with Denatured Blood Based Foam 5 different kinds of foams were evaluated concerning velocity of foam collapse:
1.) (HS 78/7) innovative foam prepared from 2 ml human whole blood heated in a 10 ml plastic syringe to 78 degrees Celsius for 7 minutes, resting in room temperature for 5 minutes, then mixed with 4 ml Aethoxysklerol 1% (Kreussler Pharma Germany) to obtain a dispersion, passed through a 200 micron filter and then foamed with room air according to the Tessari method (10× movement to and fro between two indentical syringes).

2.) (HS 78/30) same procedure as 1.) but blood sample heated for 30 minutes

3.) (blood+AE) same components as 1.) but using native human whole blood without exposure to heat >21 degrees Celsius (room temperature)

4.) (AE 2+8) standard sclerofoam like used by today's physicians prepared from 2 ml Aethoxysklerol 2% and 8 ml room air according to Tessari method.

5.) (AE2, 6+4) alternative sclerofoam containing the same volume of fluids as example 1.), but without denatured blood.

The velocity of foam collapse was measured according to the volume of fluid accumulating at the bottom of the sample syringes stored in an upright position. During decay of foam bubbles these will grow and apparently the level of foam may remain the same, but accumulating fluid is a valid indicator of foam collapse. Half-life was defined as the time passed unto half of the initial fluid volume was showing at the bottom of the syringe. Measurements were performed after minute 1, 2, 3, 4, 5, 30, 60 and 24 hours (see FIGS. 7 a-d), Tables 2 and 3.

medical use. Sample 3 showed the fastest disintegration of all foam samples with 66.6% of the used fluid volume being visible already after one minute. The half-live is <1 minute. The comparison to sample 1 proves that the increased half-life of the innovative foam is not due to the ingredients which are chemically identical (blood-sclerosant-air), but to the use of denaturized blood. Sample 4 showed disintegration of half of foamed volume at about 2 minutes (see table 2). This correlates with numerous literature date of foam half-lifes of 30-180 seconds. The comparison to sample 1 proves the large increase of half-life obtained by the invention. Sample 4 contains as much sclerosant fluid as sample 1, and the same amount of sclerosant substance. However, the decay is faster than for standard microfoam (sample 4). This result proves that the amount of fluid is not the cause for the increased half-life of the innovative foam.

Figure 8:
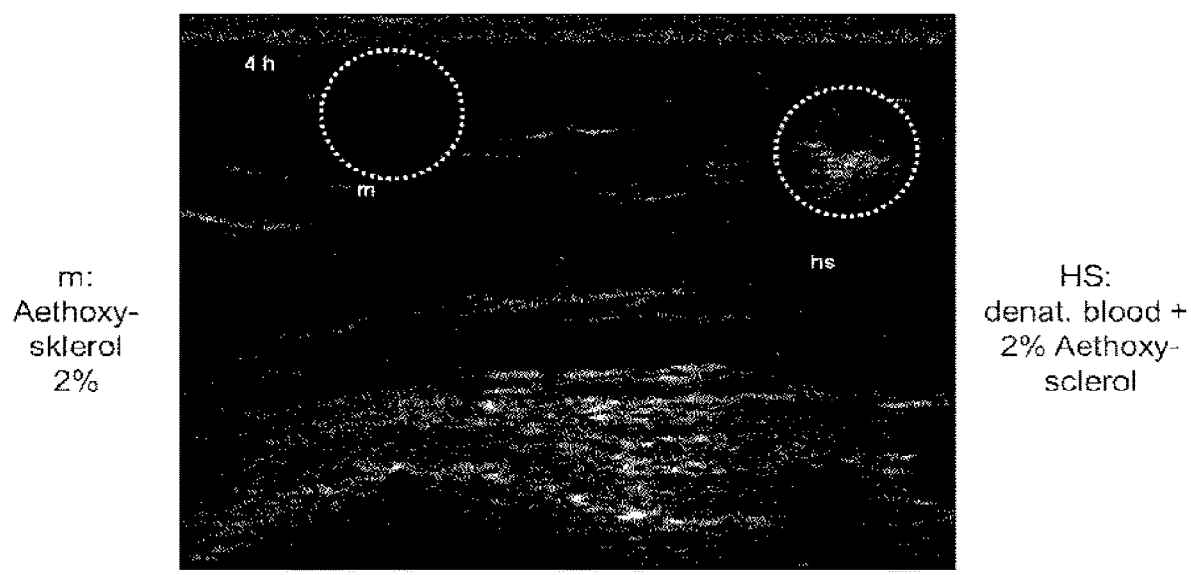

Furthermore the sclerosant drug foam according to the invention (1 in the above example) shows also a greater half live in veins, as can be seen in ultrasound images (FIG. 8) compared to regular sclerosant foam (4 in the above example).

Further properties of the sclerosant drug foam according to the present invention are shown in the following tables:

TABLE 2

Overview of tested sclerosant foams

| foam | 1<br>HS-78/7 | 2<br>HS-78/30 | 3<br>blood + AE | 4<br>AE 2 + 8 | 5<br>AE2, 6 + 4 |
|---|---|---|---|---|---|
| heated to . . . degree C. for . . . minutes | 78/7 | 78/30 | not heated | not heated | not heated |
| blood (ml) | 2 | 2 | 2 | 0 | 0 |
| sclerosant (ml) | 4 | 4 | 4 | 2 | 6 |
| concentration AE | 1 | 1 | 1 | 2 | 0.666 |
| volume AE ml | 0.04 | 0.04 | 0.04 | 0.04 | 0.03996 |
| total volume of fluid (ml) | 6 | 6 | 6 | 2 | 6 |
| total volume of gas (ml) | 4 | 4 | 4 | 8 | 4 |

TABLE 3 time dependent collapse of sclerosant foams (see also FIG. 7)

| | | foam | | | | |
|---|---|---|---|---|---|---|
| foam collapse | time/min. | 1<br>ml | 2<br>ml | 3<br>ml | 4<br>ml | 5<br>ml |
| fluid in ml indicating collapse of foam | 1 | 0.00 | nd | 4.00 | 0.00 | 1.00 |
| | 2 | 0.00 | nd | 5.80 | 1.00 | 4.00 |
| | 3 | 0.00 | nd | 6.00 | 1.50 | 5.00 |
| | 4 | 0.00 | nd | 6.00 | 2.00 | 5.25 |
| | 5 | 0.00 | nd | 6.00 | 2.00 | 5.50 |
| | 15 | 0.50 | nd | 6.00 | 2.00 | 6.00 |
| | 30 | 0.80 | nd | 6.00 | 2.00 | 6.00 |
| | 60 | 1.00 | nd | 6.00 | 2.00 | 6.00 |
| | 24 h | 1.20 | nd | 6.00 | 2.00 | 6.00 | nd = not determinable

Results: Sample 1 showed a very slow foam disintegration collecting just 1.2 ml of fluid after 24 h. Thus, the volume half-life is >24 h. Sample 2 showed a rapid disintegration of a brighter, air-containing fraction of about 50% of volume, and a darker, depositing section containing particles. The foam disintegration was assessed as "not determinable" as no fluid collection was distinguishable from the deposit. Due to the rapid formation of a large unfoamed deposit, such foam would be unacceptable for

TABLE 4

Closure of great saphenous veins 30 minutes after sclerotherapy using 1% aethoxysklerol (AE) in 20 patients, in color duplex ultrasound examinations in the standing individual.

| common foam (2 ml AE, 8 ml room air) | 1/10 | 10% |
|---|---|---|
| foam according to the intervention (1.5 ml matrix, 2 ml AE, 6.5 ml room air) | 9/10 | 90% |

Comparison of Foam Viscosity

Plastic syringes of 10 ml volume were filled with sclerosant foams a) standard, prepared with 2 ml Aethoxysklerol 1% plus 8 ml gas (30% $CO_2$+70% $O_2$) and b) a foam according to the invention prepared from 2 ml Aethoxysklerol 1%, 2 ml fresh human whole blood, 1 ml Aqua dest., and 5 ml gas (30% $CO_2$+70% $O_2$) by use of TESSARI method. The syringes were closed at the tip, opened at the other side and fixed in an inclined position of 60 degrees from horizontal. A plastic ball of 13 mm in diameter and a weight of 1.6 grams was positioned at the foam surface and released. The time of passage through the foam was recorded. The measurements were repeated five times. This setting was chosen as commercial device for measurements of viscosities is available for fluids, but not for foam.

Results: Within the standard foam, the ball moved with a mean of 1.9 cm/s while in the foam prepared with a blood-derived matrix the ball just reached a mean of 0.2 cm/s. This indicates that the viscosity of the inventive foam is much higher than in standard sclerofoams. The viscosity will depend not only on the ingredients, but also on mechanical forces when mixing.

Blood-Derived Matrix without Red Blood Cells

Common sclerofoam (2 ml Aethoxysklerol 1%+8 ml gas mixture 30% $CO_2$, 70% $O_2$) was compared to a foam according to the invention, prepared by taking a whole blood sample of 5 ml, extracting red blood cells by centrifugation at 1000 UPM for 10 minutes end then exposing a 2 ml sample to temperature of 95° C. for 5 minutes, finally foaming it with 2 ml Aethoxysklerol 1%+6 ml gas mixture 30% $CO_2$, 70% $O_2$. Both samples were foamed simultaneously according to TESSARI method and then the disintegration of the foams was observed for 30 minutes. Results: The half-live, measured according to accumulating fluid at the bottom of the sample vessels, was 2.5 minutes for standard and 27.5 minutes for the inventive foam. Thus, the obtained increase of half-live is less than achieved with a foam prepared on whole blood basis, but still significantly superior to common sclerofoam. A foam with reduced contents of red blood cells may be used in superficial veins to avoid discolorations. As in foams of this kind no red blood cells are present to indicate appropriate denaturation, all parameters (temperature, time, sample geometry) were chosen identical to the experience of whole-blood containing samples.

FIGURE CAPTIONS

FIG. 1, a-b: ultrasound scan of a varicose vein after injection of polidocanol microfoam, a: longitudinal view, b: cross-sectional view. The contents of sound reflecting gas is responsible for the visibility of the foam column, but also for the formation of acoustic shadows (arrows) which hide valuable information.

FIG. 2 *a-b*: Ultrasound images after application of a foam according to the invention, a) longitudinal and b) cross-sectional. The foam deposit is clearly visible (arrows), but transparent to ultrasound to a large extent.

FIG. 3 *a-c*: Comparison of common white sclerofoams (M2, GM7-04) prepared with 2 ml Aethoxysklerol 2% plus 8 ml room air according to Tessari Method (M2) resp. 2 ml Aethoxysklerol 2%, 2 ml glucose 70% plus 6 ml room air according to Tessari Method 2% (GM7-04), to a sclerofoam according to the invention (HS2) prepared with 2 ml denatured blood matrix, 2 ml Aethoxysklerol 2% and 6 ml room air. Due to the contents of denatured whole blood, the color of this sample is brownish. The clock shows the time after mixing. In the common sclerofoam, disintegration is even visible at the bottom of the vessels after 30 seconds (a) and has reached 15-20% after 90 seconds (b), corresponding to an assumed half-life of up to 210 seconds. In this sample the improved foam is still stable after 4 hours with partially enlarged bubbles but disintegrated fluid parts of less than 15% (c).

FIG. 4 *a-d*: Due to its higher stiffness or viscosity, the foam can be distributed within veins very precisely. This is demonstrated in vitro using transparent tubes showing common foam (Aethoxysklerol 1%, 2 ml, plus 8 ml filtrated room air, 100 s post mixing) in a) vertical and b) inclined tube position, compared to foam according to the invention (Aethoxysklerol 1%, 2 ml, 2 ml denatured blood matrix, plus 6 ml filtrated room air, at 100 s post mixing), c) vertical and d) even horizontal tube position. Common foam distributes diffuse and wedge-shaped (b), the curves in the foam border are due to inhomogenous non-stick coating of the test tubes. The invented foam forms a distinct rectangular border line at any spatial orientation of the test tubes (c,d).

Figure 5A:
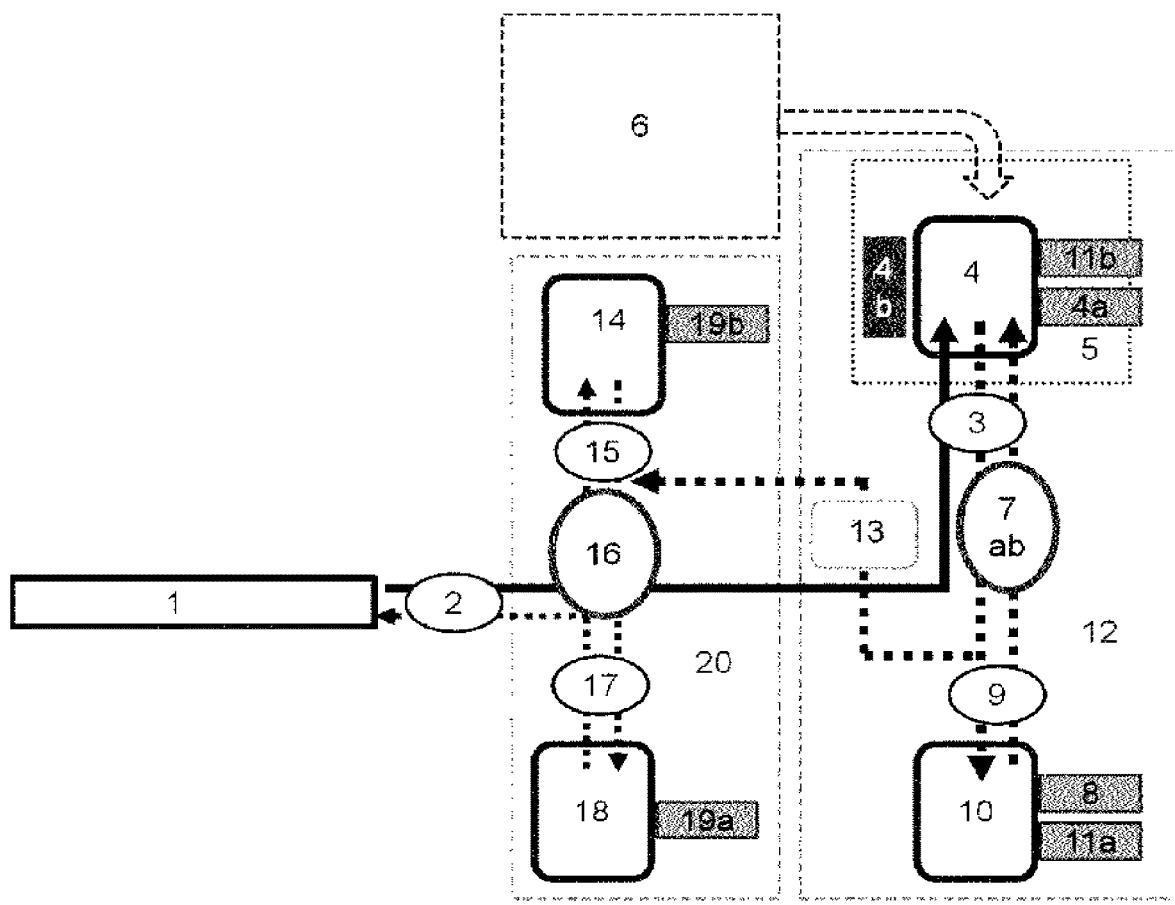
Figure 5B:
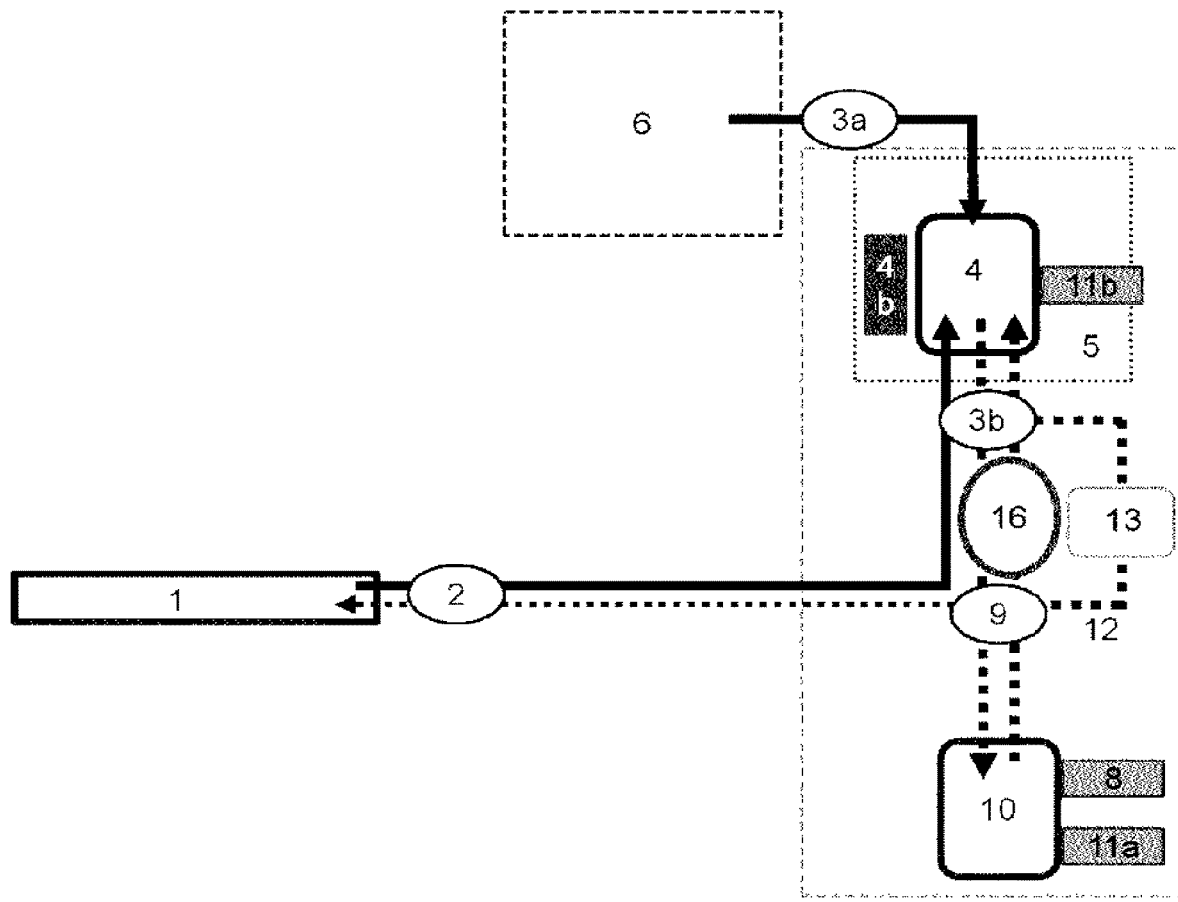

FIG. 5*a*: Scheme of a device to prepare injectable sclerofoam using a matrix based on autologous blood, using a catheter (1) with input-output switch (IOS, 2) wherein IOS may either be two-way stopcocks or pairs of single stopcocks, connected to first container (4) which is adapted to an integral or exchangeable heat providing and/or heat transferring unit (6). The suitable degree of blood denaturation is determined by a detector system (4*b*) attached to the heat-denaturing unit (5) which is connected via optional IOS (3, 9) to a second container (10) while integrating a dispersing means (7*a*), optionally with a cutting device (7*b*). Optional connectors for external supply of fluid or sclerosant (8), for rinsing or to apply positive or negative pressure (11*a*, 11*b*, 19*a*, 19*b*) may be added in suitable locations related to containers 4 or 10. The dotted lines may represent a single passage from (4) to (10), or multiple to- and fro passages. The containers (4) and (10) and related IOS and connectors may be summarized as denaturing and dispersing unit (12).

The dispersion is optionally passed through a filter element (13) to the foaming unit (20), consisting of a container to hold the dispersion (14), a container to contain a medical gas (18) and a means to apply mechanical force or energy (16). Furthermore, IOS (15, 17) and a means to externally supply a medical gas (19).

The lines connecting the containers indicate flow of blood (fat line), dispersion (fat dotted line), and foam (small dotted line).

FIG. 5*b*: Blood denaturation may also be performed by use of heated fluid or steam. In this case, a heating element (6) is attached to one of the containers to provide heated fluid, heated sclerosant and/or steam resp. heated gas, and the heated substance is guided to the denaturation container (4).

Figure 5C:
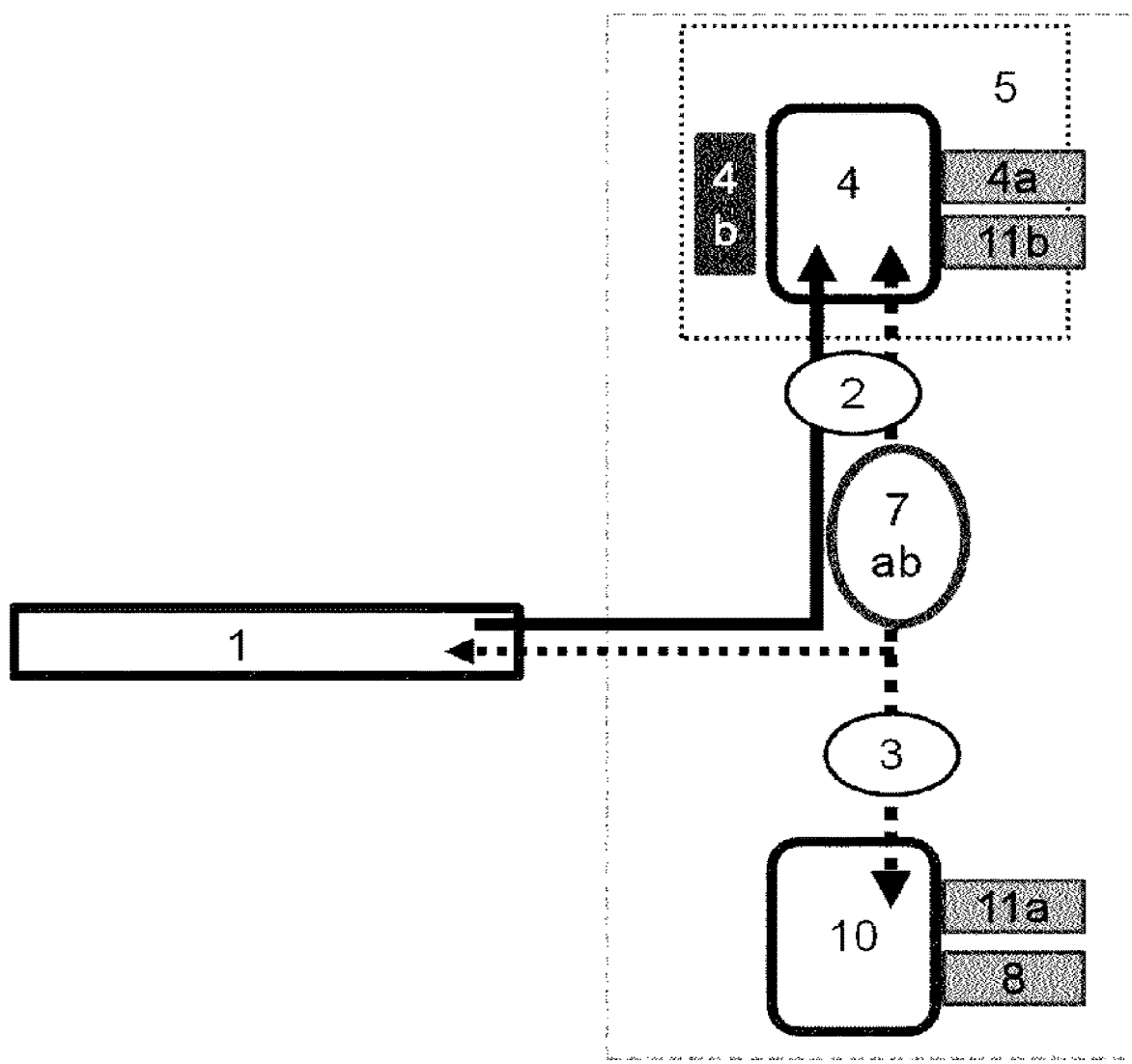

FIG. 5*c*: For simplification, the foaming unit (20) may be replaced by the containers and other elements of unit (12), not using a filter element (13) or providing it as an option in a switched bypass array connecting containers (4) and (10), and using auxilliary access points (8, 11) to supply a medical gas.

FIG. 6: Heat-denatured blood forming an inherent solid body, in this example comparing samples prepared in a syringe at procedural temperatures of 80 and 95° C. and spread on a tissue.

FIG. 7: Comparison of the stability of a sclerosant drug foam according to the invention at different time points after generation 7*a*) 1 min, 7*b*) 3 min, 7*c*) 30 min, 7*d*) 24 h FIG. 8: Ultrasound comparison of regular sclerosant foam and foam according to the present invention. A common sclerosant foam prepared with 2 ml Aethoxysklerol 1% and 8 ml room air according to Tessari method was injected to fill a branched human vein of 5 mm in diameter (m), and a sample of the inventive foam prepared from 1 ml denatured whole blood was injected to fill a parallel segment of the same vein with 5 mm diameter (hs). After 4 hours, ultrasound showed no residual common foam (m), while the inventive foam is still present (hs).

Figure 9A:
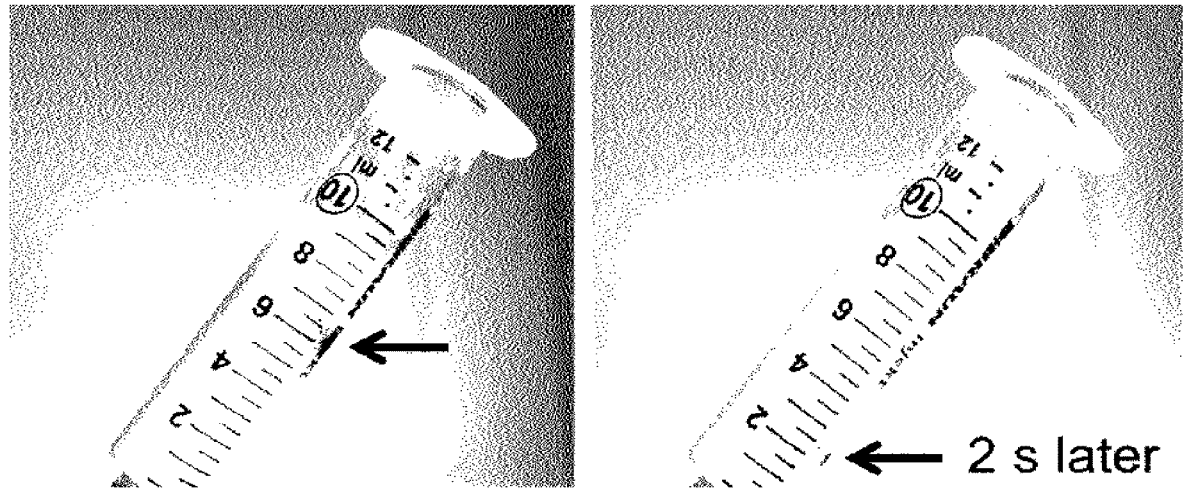
Figure 9B:
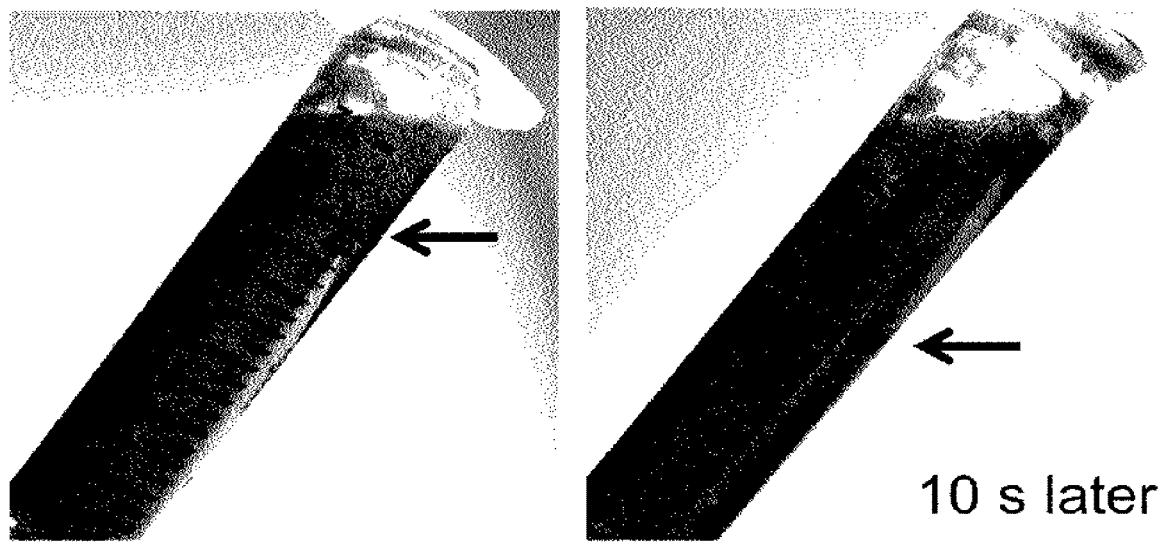

FIG. 9: Ball test measurement of viscosity of common sclerosant foam (9*a*) and new sclerosant foam according to the present invention (9*b*).

The invention claimed is:
1. A device for the production of a sclerosant drug foam comprising:
 a) a catheter for blood sampling and foam distribution,
 b) a first container for blood collection and denaturation, c) an external element for denaturation by heat, radiation or chemicals to be physically or thermically connected to the first container, and d) at least one sclerosant agent.

2. The device according to claim 1, wherein the first container is a cylindrical polyethylene container with 3 mm inner diameter and 3.4 mm outer diameter.

3. The device of claim 1, further comprising
a unit to apply mechanical force to the contents of the first container for mixing/dispersing, or
a combination of a unit to apply mechanical force to the contents of the first container for mixing/dispersing and a chopping element.

4. The device according to claim 1, wherein all the components except the catheter have an outer diameter of below 30 mm.

5. The device according to claim 1, wherein the device is modular.

6. The device according to claim 1, wherein the device is integral.

7. The device according to claim 1, wherein one or more containers is a syringe.

8. The device of claim 1, further comprising a second container for at least one fluid and/or at least one sclerosant agent.

9. The device of claim 8, further comprising
a unit to apply mechanical force to the contents of the second container for mixing/dispersing, or
a combination of a unit to apply mechanical force to the contents of the second container for mixing/dispersing and a chopping element.

10. The device according to claim 9, wherein the filter element removes all particles exceeding a size of greater than 120 μm.

11. The device of claim 8, further comprising a filter element and a third container to hold the dispersion.

12. The device according to claim 11, wherein the containers are modular or integral.

13. The device of claim 11, further comprising a unit to apply mechanical force to the contents of the third container for foaming.

14. The device according to claim 13, wherein the containers, connection elements, switches and filter elements, chopping elements and foaming elements are provided as single parts to be assembled by the user under sterile conditions prior to use or as a one-way system except the external unit for physical denaturation.

15. The device according to claim 11, further comprising a fourth container containing a medical gas.

16. The device according to claim 15, wherein the external element for heating/denaturation, unit for dispersing and unit for foaming are modular.

17. The device of claim 15, further comprising a unit to apply mechanical force to the contents of the fourth container for foaming.

18. The device of claim 17, further comprising one or more of:
i. two-ways switches, one-way valves, single stop cocks or combinations thereof,
ii. auxiliary access to the device to apply negative or positive pressure, or to supply fluids or gases, and
iii. connection elements connecting all modular parts.

19. The device according to claim 3, wherein the chopping element comprises at least one cutting edge, which is used to chop particles of partially denatured blood, several cutting edges located within a connecting tube structure, wherein the cutting edges are arranged to face the particle inflow and cover less than 10% of the tube cross-section area.

20. The device of claim 1, further comprising:
e) a second container for at least one fluid and/or at least one sclerosant agent, and/or
f) a unit to apply mechanical force to the contents of the first and/or second container for mixing/dispersing, and/or
g) a chopping element, and/or
h) a filter element, and/or
i) a third container to hold a dispersion, and/or
j) a fourth container containing a medical gas, and/or
k) a unit to apply mechanical force to the contents of the third and/or fourth container for foaming, and/or
l) two-ways switches, one-way valves, single stop cocks or combinations thereof, and/or
m) auxiliary access to the device to apply negative or positive pressure, or to supply fluids or gases, and/or
n) connection elements connecting the parts a) to m).

21. A method for treating insufficient veins comprising the steps of:
i) accessing the diseased vein;
ii) preparing a sclerosant drug foam on a basis of denatured blood; and
iii) deploying the sclerosant drug foam along a diseased vein
wherein the steps of i)-iii) are carried out by using the device according to claim 1.

* * * * *